United States Patent
Kaye et al.

(10) Patent No.: US 10,606,984 B1
(45) Date of Patent: Mar. 31, 2020

(54) ADHERENCE MONITORING SYSTEM

(71) Applicant: McKesson Corporation, Irving, TX (US)

(72) Inventors: Elizabeth S. Kaye, Suwanee, GA (US); Stacy Hopkins, Loganville, GA (US); Jeremiah Rothschild, Roswell, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 503 days.

(21) Appl. No.: 15/084,019

(22) Filed: Mar. 29, 2016

(51) Int. Cl.
*G06F 19/00* (2018.01)
*G16H 10/60* (2018.01)

(52) U.S. Cl.
CPC ......... *G06F 19/3456* (2013.01); *G16H 10/60* (2018.01)

(58) Field of Classification Search
CPC .. G06F 19/3456; G06F 19/3475; G06F 19/30; G06F 19/32; G06F 19/34; G16H 10/60; G16H 20/60; G16H 20/70; G16H 20/90; G06Q 50/22; G06Q 50/24
See application file for complete search history.

(56) References Cited

U.S. PATENT DOCUMENTS

| | | | |
|---|---|---|---|
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,237,620 A | 8/1993 | Deaton et al. | |
| 5,305,196 A | 4/1994 | Deaton et al. | |
| 5,327,508 A | 7/1994 | Deaton et al. | |
| 5,388,165 A | 2/1995 | Deaton et al. | |

(Continued)

FOREIGN PATENT DOCUMENTS

| CA | 2482370 | 3/2006 |
|---|---|---|
| WO | WO 1995003569 | 2/1995 |

(Continued)

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

(Continued)

*Primary Examiner* — Michael Tomaszewski
*Assistant Examiner* — Mohmad Muqueeth
(74) *Attorney, Agent, or Firm* — Alston & Bird LLP

(57) ABSTRACT

An improved adherence monitoring system increases the efficiency for obtaining patient adherence information. The improved adherence monitoring system reduces network traffic with regards to the communication of patient adherence information. The improved adherence monitoring system automates an adherence notification pathway. The improved adherence monitoring system can increase patient adherence by increasing the efficiency of medication therapy. The improved adherence monitoring system may also increase the efficiency by which patient adherence information is disbursed.

19 Claims, 11 Drawing Sheets

(56) References Cited

U.S. PATENT DOCUMENTS

| | | | |
|---|---|---|---|
| 5,430,644 A | 7/1995 | Deaton et al. |
| 5,448,471 A | 9/1995 | Deaton et al. |
| 5,588,649 A | 12/1996 | Blumberg et al. |
| 5,592,560 A | 1/1997 | Demon et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,915,007 A | 6/1999 | Klapka |
| 5,926,795 A | 6/1999 | Williams |
| 5,970,469 A | 10/1999 | Scroggie et al. |
| 5,974,399 A | 10/1999 | Giuliani et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardensvvartz et al. |
| 6,067,069 A | 5/2000 | Krause |
| 6,067,524 A | 5/2000 | Byerly et al. |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,958 B1 | 10/2001 | Deaton et al. |
| 6,321,210 B1 | 11/2001 | O'Brien et al. |
| 6,334,108 B1 | 12/2001 | Deaton et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,484,146 B2 | 11/2002 | Day et al. |
| 6,578,003 B1 | 6/2003 | Camarda et al. |
| 6,584,448 B1 | 6/2003 | Laor |
| 6,684,195 B1 | 1/2004 | Deaton et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,885,994 B1 | 4/2005 | Scroggie et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,155,397 B2 | 6/2006 | Alexander et al. |
| 7,225,052 B2 | 5/2007 | Foote et al. |
| 7,227,842 B1 | 6/2007 | Ji et al. |
| 7,228,285 B2 | 6/2007 | Hull et al. |
| 7,233,913 B2 | 6/2007 | Scroogie et al. |
| 7,309,001 B2 | 6/2007 | Banfield et al. |
| 7,415,426 B2 | 8/2008 | Williams et al. |
| 7,426,480 B2 | 9/2008 | Granger et al. |
| 7,630,908 B1 | 12/2009 | Amrien et al. |
| 7,734,483 B1 * | 6/2010 | Smith ............... G06F 19/328 |
| | | 705/3 |
| 7,957,983 B2 | 6/2011 | Hoffman et al. |
| 8,032,393 B2 | 10/2011 | Palazzolo et al. |
| 8,036,913 B1 * | 10/2011 | Pinsonneault ........ G06F 19/328 |
| | | 705/2 |
| 2002/0002495 A1 | 1/2002 | Ullman |
| 2002/0087583 A1 | 7/2002 | Morgan et al. |
| 2002/0111832 A1 | 8/2002 | Judge |
| 2002/0165736 A1 | 11/2002 | Tolle et al. |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0074218 A1 | 4/2003 | Liff et al. |
| 2003/0125986 A1 | 7/2003 | Collosi |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich et al. |
| 2004/0039599 A1 | 2/2004 | Fralic |
| 2004/0054657 A1 | 3/2004 | Takeyama |
| 2004/0073457 A1 | 4/2004 | Kalies et al. |
| 2004/0078234 A1 | 4/2004 | Tallal, Jr. et al. |
| 2004/0107117 A1 | 6/2004 | Denny |
| 2004/0111277 A1 | 6/2004 | Pearson et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0249745 A1 | 12/2004 | Baaren |
| 2005/0015280 A1 | 1/2005 | Gabel et al. |
| 2005/0033610 A1 | 2/2005 | Cunningham |
| 2005/0060201 A1 | 3/2005 | Connely, III et al. |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0154627 A1 | 7/2005 | Zuzek et al. |
| 2005/0171815 A1 | 8/2005 | Vanderveen |
| 2005/0187790 A1 | 8/2005 | Lapsker |
| 2005/0187793 A1 | 8/2005 | Myles |
| 2005/0187821 A1 | 8/2005 | Lapsker |
| 2005/0197862 A1 | 9/2005 | Paterson et al. |
| 2005/0240442 A1 | 10/2005 | Lapsker |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0149587 A1 | 7/2006 | Hill, Sr. et al. |
| 2006/0149784 A1 | 7/2006 | Tholl et al. |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0259363 A1 | 11/2006 | Jhetam et al. |
| 2006/0271398 A1 | 11/2006 | Belcastro |
| 2006/0271402 A1 | 11/2006 | Rowe et al. |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0088576 A1 | 4/2007 | de Beus et al. |
| 2007/0097792 A1 | 5/2007 | Burrows et al. |
| 2007/0124177 A1 | 5/2007 | Engleson et al. |
| 2007/0136100 A1 | 6/2007 | Daugherty et al. |
| 2007/0174092 A1 | 7/2007 | Lara et al. |
| 2007/0179957 A1 | 8/2007 | Gibson et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2009/0164376 A1 | 6/2009 | Guthrie |
| 2011/0161109 A1 | 6/2011 | Pinsonneault et al. |
| 2011/0196700 A1 | 8/2011 | Sekura |
| 2013/0311205 A1 * | 11/2013 | Creswell ............ G06F 19/3475 |
| | | 705/3 |
| 2015/0269695 A1 * | 9/2015 | Pinsonneault ..... G06Q 30/0207 |
| | | 705/2 |
| 2015/0371000 A1 | 12/2015 | Pinsonneault |

FOREIGN PATENT DOCUMENTS

| | | |
|---|---|---|
| WO | WO 2000039737 | 7/2000 |
| WO | WO 2007/025295 | 3/2007 |

OTHER PUBLICATIONS

Anonymous, Medic: On-line Goes In-House, Chain Store Age Executive, Jan. 1987, pp. 128-132. vol. 63, Issue 1, USA.

(56) References Cited

OTHER PUBLICATIONS

Anonymous, Pharmacy Industry Leaders Launch Firm to Supply Real-Time Data. PR Newswire. Jul. 30, 2001, page New York, NY, USA.

Anonymous, TechRx Announces Successful Beta Deployment of T-Rex. PR Newswire. May 13, 2002.

Final Office Action for U.S. Appl. No. 13/833,698 dated Jul. 30, 2015.

Final Office Action for U.S. Appl. No. 13/833,929 dated Oct. 8, 2015.

Hess, Lisa M., et al. "Measurement of adherence in pharmacy administrative databases: a proposal for standard definitions and preferred measures." Annals of pharmacotherapy 40.7-8 (2006): 1280-1288.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Non-Final Office Action for U.S. Appl. No. 13/833,698 dated Jan. 29, 2015.

Non-final Office Action for U.S. Appl. No. 13/833,929 dated Feb. 13, 2015.

Office Action for Canadian Application No. 2,723,350 dated Feb. 21, 2018, 4 pages.

Office Action for U.S. Appl. No. 12/650,759 dated Aug. 5, 2014, 5 pages.

Office Action for U.S. Appl. No. 12/650,759 dated Aug. 21, 2015, 12 pages.

Office Action for U.S. Appl. No. 12/650,759 dated Feb. 9, 2015, 6 pages.

Office Action for U.S. Appl. No. 12/650,759 dated Jan. 27, 2012, 16 pages.

Office Action for U.S. Appl. No. 12/650,759 dated Jul. 17, 2012, 19 pages.

Office Action for U.S. Appl. No. 12/650,759 dated Nov. 12, 2013, 20 pages.

Office Action for U.S. Appl. No. 14/312,471 dated Apr. 28, 2017, 27 pages.

Office Action for U.S. Appl. No. 14/312,471 dated Apr. 29, 2019, 22 pages.

Office Action for U.S. Appl. No. 14/312,471 dated Aug. 2, 2018, 32 pages.

Office Action for U.S. Appl. No. 14/312,471 dated Oct. 16, 2017, 31 pages.

Poston, J. W., Loh, E. A., & Dunham, W. (1999). The medication use study: A large-scale controlled evaluation of the effects of the vital interests program on adherence to medication regimens. CPJ. Canadian Pharmaceutical Journal, 131(10), 30-38. Retrieved from http://search.proquest.com/docview/221172694?accountid=14753.

Sampson, R.J., Taking Control of Health Care Costs, Best's Review— Life Health Insurance Edition, Nov. 1983, 64-66, vol. 84, Issue 7, USA.

\* cited by examiner

ADHERENCE MONITORING SYSTEM

TECHNICAL FIELD

Aspects of the disclosure relate generally to adherence monitoring, and more particularly, to an improved adherence monitoring system.

BACKGROUND

A healthcare provider, such as a physician, doctor's office, urgent care center, hospital, or the like provides numerous healthcare related products and services to patients, including providing prescription products (e.g., medications, devices, etc.). However, the healthcare provider generally does not receive information with regard to whether the prescribed medication and/or product were actually picked up by the patient. While the typical prescription request format does include an option to provide a fill status solution, the selection requires a manual intervention by a pharmacist and adds unnecessary network traffic. This type of manual process is cumbersome and generally does not derive a direct benefit to the pharmacy. Furthermore, the fill status option of a NCPDP Telecom standard formatted request typically requires vendor system support, providing additional overhead for the vendor. As a result, the fill status option in the typical prescription request is an unreliable option, and therefore not valued by the physician. An improved adherence monitoring system may reduce or eliminate certain issues related to monitoring patient adherence with regards to medication therapy.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Figure 1A:
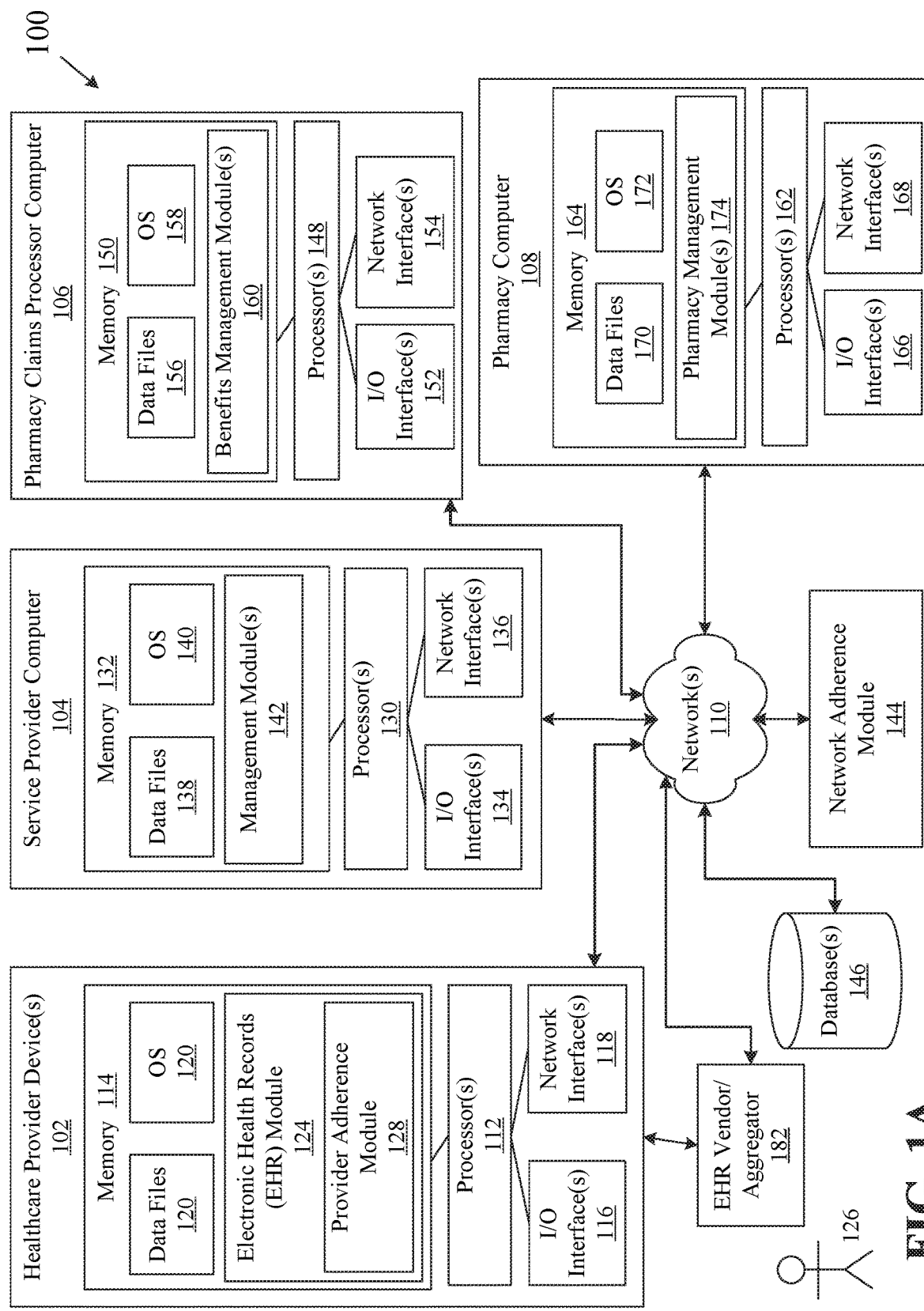
FIGS. 1A and 1B illustrates an example overview of a system that facilitates the improved adherence monitoring for patient according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include an improved adherence monitoring system. In some example implementations, a prescription benefit check request may be communicated from a healthcare provider to a service provider via an electronic health records intermediary. In response to the prescription benefit check request, a prescription fill notification request may be generated. The prescription fill notification request may be generated manually by a prescriber, automatically by an EHR system associated with a prescriber device, or may be communicated to the service provider by a vendor associated with the EHR intermediary. The generation of the prescription fill notification request may be based upon, without limitation, a medication and/or product of a specific class (e.g., a schedule I drug), a patient diagnosis (e.g., a high blood pressure diagnosis), a specific prescriber type (e.g., gynecologist, neurologist, etc.), a prescriber location (e.g., state, city, county, etc.), and/or a prescriber's practice size (e.g., large clinic, small clinic, multi prescriber clinic, single prescriber clinic, etc.). In addition, the prescription fill notification request may also include information indicating whether the prescription fill notification request is a first fill adherence request only, or if the prescription fill notification request is an adherence request corresponding to all prescriptions, initial fill as well as any and all refills associated with a prescription.

The service provider may monitor a network to determine whether billing request/response information is available for the medication/patient identified in the prescription benefit check request. For example, the determination may be based upon a matching algorithm utilizing a prescriber ID, patient ID, patient gender, patient date of birth, patient zip code, and/or service ID identified in the prescription benefit check request. The service provider may monitor the network for a specific period of time. Where the service provider identifies an approved or paid prescription request for the identified medication and/or patient identified in the prescription benefit check request, the service provider may communicate the identified information to the healthcare provider via the EHR intermediary. Where the specified period of time has expired, and no paid or approved prescription request has been identified, the prescription fill notification request may expire. The expiration of the prescription fill notification request and/or the absence of a paid or approved prescription request may be communicated to the healthcare provide via the EHR intermediary.

In addition, the service provider may generate a medication adherence report. For example, an adherence report may be generated for a particular prescriber, a particular patient, a fill rate for all patients associated with a particular prescriber, a fill rate for a therapeutic drug class, an adherence level request based upon patient pay amount (e.g., patient co-pay), and the like. By way of another example, an adherence report may be generated based upon one or more search parameters set by an EHR vendor. In one example, the EHR vendor may be associated with the EHR intermediary. The information collected by the service provider may be communicated to the EHR vendor for distribution to the healthcare provider, the pharmacy claims processor, or the pharmacy via the EMR intermediary.

System Overview

Figure 1B:
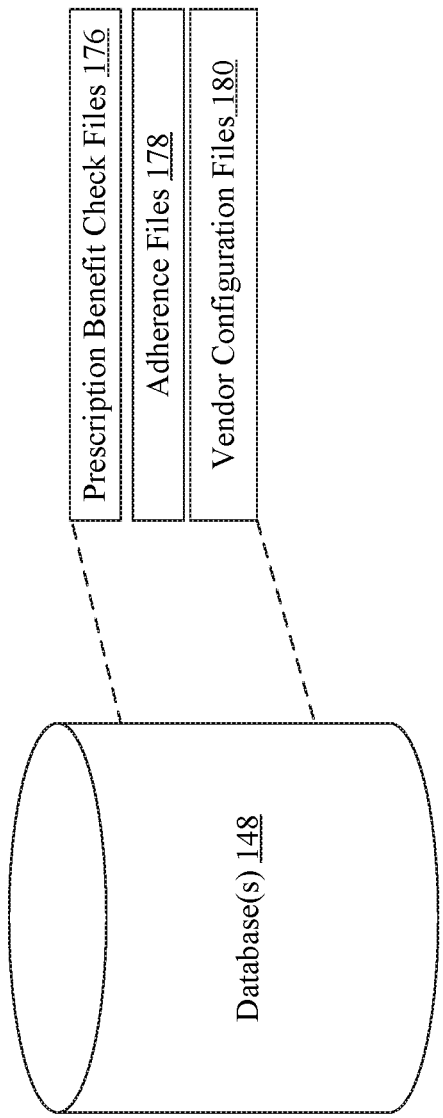

FIG. 1 illustrates an example system 100 supporting the improved adherence monitoring system, according to an example embodiment. As shown in FIG. 1, the system 100 may include at least one healthcare provider devices 102, service provider computers 104, pharmacy claims processor computer 106, pharmacy computer 108, network adherence module 144, and/or an EHR vendor/aggregator 182. As desired, each of the healthcare provider device 102, service provider computer 104, network adherence module 144, pharmacy claims processor computer 106, and/or pharmacy computer 108 may include one or more processing devices that may be configured for accessing and reading associated computer-readable media having stored thereon data and/or computer-executable instructions for implementing the improved adherence monitoring system.

Additionally, in certain exemplary embodiments, the service provider computer 104 and/or the network adherence module 144 may be in communication with one or more data storage devices, such as a database 146. The database 146 may receive, store, and provide, as needed, patient data and/or prescription data from the service provider computer 104 and/or the network adherence module 144. In certain exemplary embodiments, the prescription request data includes all or any portion of the data included in prescription requests received by the service provider computer 104 from a healthcare provider device 102 and/or processed prescription request responses processed by a pharmacy claims processor computer 106 or a pharmacy computer 108. Alternatively, the data storage function may be included in the service provider computer 104 and/or the patient copay assistance module 146 themselves, such as in the memory 130 of the service provider computer 104.

Generally, network devices and systems, including one or more of the healthcare provider devices 102, service provider computers 104, network adherence module 144, pharmacy claims processor computer 106, and pharmacy computer 108 may include or otherwise be associated with suitable hardware and/or software for electronically transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices forms a special purpose computer or particular machine. As used herein, the term "computer-readable medium" describes any form of suitable memory or memory device.

As shown in FIG. 1, the healthcare provider device 102, service provider computer 104, pharmacy claims processor computer 106, pharmacy computer 108, network adherence module 144, database 146, and EHR vendor/aggregator 182 may be in communication with each other via one or more networks, such as network 110, which as described below can include one or more separate or shared private and public networks, including the Internet or a publicly switched telephone network. Each of these components, the healthcare provider device 102, service provider computer 104, pharmacy claims processor computer 106, pharmacy computer 108, network adherence module 144, database 146, EHR vendor/aggregator 182, and the network 110 will now be discussed in further detail.

Each healthcare provider device 102 may be associated with (e.g., located within and/or providing computing services for) a prescriber or other healthcare provider, such as, for example, a physician, physician's office, hospital, clinic, etc. Each healthcare provider device 102 may be any suitable processor-driven device that facilitates the processing of prescription benefit check requests made by or on behalf of a physician office for a patient prescription, the communication of healthcare requests to the service provider computer 104 via the EHR vendor/aggregator 182, and/or the receipt, processing, and display of responses received from the service provider computer 104 via the EHR vendor/aggregator 182. For example, the healthcare provider device 102, may be a computing device that includes any number of a server computers, a mainframe computers, one or more networked computers, a desktop computer, a personal computer, a digital assistant, a personal digital assistant, a digital tablet, an Internet appliance, an application-specific circuit, microcontroller, minicomputer, or any other processor-based device. The execution of the computer-implemented instructions by the healthcare provider computer 102 forms a special-purpose computer or other particular machine that is operable to facilitate the processing of prescription benefit check made by or on behalf of the physician's office and the communication of information associated with prescription benefit check requests to a healthcare provider device 102. Additionally, in certain example embodiments, the operations and/or control of each healthcare provider device 102 may be distributed amongst several processing components.

In addition to having one or more processors 112, each healthcare provider device 102 may include one or more memory devices 114, one or more input/output ("I/O") interfaces 116, and one or more network interfaces 118. The memory devices 114 may be any suitable memory device, for example, caches, read-only memory devices, random access memory devices, magnetic storage devices, removable storage devices, etc. The memory devices 114 may store data, executable instructions, and/or various program modules utilized by the healthcare provider device 102, for example, data files 120, an operating system ("OS") 122, and/or an electronic health records (EHR) module 124, respectively. The data files 120 may include any suitable data that facilitates the receipt and/or processing of prescription benefit check requests by the healthcare provider device 102 and the generation and/or processing of prescription benefit check requests that are communicated to the service provider computer 104. For example, the data files 132 may include, but are not limited to, healthcare information and/or contact information associated with one or more patients, information associated with the particular healthcare provider and/or the respective healthcare provider device 102, information associated with the service provider computer 104, information associated with one or more vendors (e.g., an EHR vendor), and/or information associated with one or more prescription benefit check requests. The OS 122 may be any suitable software module that controls the general operation of the healthcare provider computer 102. The OS 122 may also facilitate the execution of other software modules by the one or more processors 112, for example, the EHR module 124. The OS 122 may be any currently existing or future-developed operating system including, but not limited to, Microsoft Windows®, Apple OSX™, Linux, Unix, or a mainframe operating system.

The EHR module 124 may be a software application(s), including, but not limited to, a dedicated program: for making diagnoses, for determining prescriptions, over-the-counter medications, products or other healthcare services associated with one or more diagnoses; for creating prescription requests (including e-prescription requests (e.g., electronic prescription order requests, e-script, or e-prescription)); for reading and or updating medical records, as well as interacting with the service provider computer 104. For example, a user 126, such as a healthcare system employee, may utilize the EHR module 124 during a patient visit, for capturing the patient's pharmacy benefit information. Furthermore, the healthcare provider device 102 may utilize the EHR module 124 to retrieve or otherwise receive data, messages, or responses from the service provider computer 104 and/or other components of the system 100.

During the prescription process, the EHR module 124 may engage the provider adherence module 128 to communicate prescription information to the service provider computer 104 for use in determining whether a patient prescription has been filled and displaying the retrieved information to the prescriber. The provider adherence module 128 may gather all the required and available optional data including, but not limited to, the medication information, (e.g., total number of medications, medication name(s), NDC number(s), RxNorm medication identifiers, etc.), patient information (e.g., patient first and/or last name, gender, date of birth), and prescriber identification number (e.g., prescriber ID ((e.g., National Provider Identifier (NPI) number and/or a provider identification issued by the Drug Enforcement Agency (DEA), prescriber name, vendor (e.g., EHR vendor/aggregator 182) identification, and prescriber ZIP code or other postal zone identifier. Following the information collection, the provider adherence module 128 formats one or more prescription requests (e.g., a predetermination of benefits requests) for a patient prescription according to NCPDP Telecom standards in the agreed upon format. The one or more prescription requests may be sent to the service provider computer 104 via the EHR vendor/aggregator 182.

The one or more I/O interfaces 116 may facilitate communication between the healthcare provider device 102 and one or more input/output devices, for example, one or more user interface devices, such as, a display, keypad, keyboard, control panel, touch screen display, remote control, mouse, microphone, etc. that facilitate user interaction with the healthcare provider device 102. For example, the one or more I/O interfaces 116 may facilitate entry of information associated with a prescription benefit check request by a healthcare provider such as a physician. The one or more network interfaces 118 may facilitate connection of the healthcare provider device 102 to one or more suitable networks, for example, the network 110 illustrated in FIG. 1. In this regard, the healthcare provider device 102 may electronically receive and/or communicate information via the EHR vendor/aggregator 182 to other network components of the system 100, such as the service provider computer 104.

With continued reference to FIG. 1, the service provider computer 104 may include, but is not limited to, any suitable processor-driven device that is configured for receiving electronically, processing, and fulfilling requests from the one or more healthcare provider devices 102, the pharmacy claims processor computers 106, and/or the pharmacy computer 108. In certain exemplary embodiments, the service provider computer 104 may be a switch/router that routes prescription requests from a pharmacy to a pharmacy claims processor computer 106. For example, the service provider computer 104 may route prescription requests to a pharmacy claims processor computer 106, such as a pharmacy benefits manager (PBM), an insurer, a Medicare payor, other governmental healthcare insurance payor, or other third-party payor.

In certain embodiments, the service provider computer 104 may include a suitable host server, host module, or other software that facilitates the receipt of a prescription benefit check request from a healthcare provider device 102 and/or the routing of the prescription request to a pharmacy claims processor computer 106 or a pharmacy computer 108. Any number of healthcare provider devices 102, network adherence modules 144, databases 146, pharmacy claims processor computers 106, and/or pharmacy computers 108 may be in communication with the service provider computer 104, via the network 110 for example, as desired in various embodiments.

The service provider computer 104 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors 130 associated with the service provider computer 104 to form a special purpose computer or other particular machine that is operable to facilitate the receipt, routing, and/or processing of prescription benefit check requests and prescription requests. The one or more processors 130 that control the operations of the service provider computer 104 may be incorporated into the service provider computer 104 and/or in communication with the service provider computer 104 via one or more suitable networks. In certain exemplary embodiments, the operations and/or control of the service provider computer 104 may be distributed amongst several processing components.

Similar to the healthcare provider device 102 described above, the service provider computer 104 may include one or more processors 130, one or more memory devices 132, one or more input/output ("I/O") interfaces 134, and one or more network interfaces 136. The one or more memory devices 132 may be any suitable memory devices, for example, caches, read only memory devices, random access memory devices, magnetic storage devices, removable memory devices, etc. The one or more memory devices 132 may store data, executable instructions, and/or various program modules utilized by the service provider computer 104, for example, data files 138, an operating system ("OS") 140, a management module 142 to facilitate management of data files 138 and other data stored in the memory devices 132. The OS 138 may be a suitable software module that controls the general operation of the service provider computer 104 and/or that facilitates the execution of other software modules. The OS 138 may be any currently existing or future-developed operating system including, but is not limited to, Microsoft Windows®, Apple OSX™, Linux, Unix, or a mainframe operating system.

According to one exemplary embodiment, the data files 138 may store prescription request records and prescription benefit check request records associated with communications electronically received from various healthcare provider devices 102, and/or various pharmacy claims processor computers 106, and/or various pharmacy computers 108. The data files 138 may also store any number of suitable routing tables that facilitate determining the destination of communications electronically received from a healthcare provider device 102, pharmacy claims processor computer 106, and/or a pharmacy computer 108. In certain example embodiments, the data discussed herein that is included in the database 146 may alternatively be stored and accessed from the data files 138. The exemplary data files 138 may also store records containing, for example, patient identification data, prescription requests, tables identifying pharmacies, prescribed product (e.g., medications, devices, etc.) or service identifiers, override codes, payor identifiers, and request type codes.

The management module 142 may be operable to perform one or more pre-edits or pre-analysis on a received prescription request prior to routing or otherwise electronically communicating the received prescription request, such as a prescription claim request, predetermination of benefits request, or prescription billing request, to a suitable pharmacy claims processor computer 106 or a suitable pharmacy computer 108. Additionally, the management module 142 may be operable to perform one or more post-edits on a processed response that is electronically received from a pharmacy claims processor computer 106 for a prescription request prior to routing the processed prescription response to one of the healthcare provider devices 102. In one example embodiment, the management module may be operable to parse the prescription request and/or processed prescription request response to determine one or more of the pharmacy identifier, prescribed product (e.g., medications, devices, etc.) or vendor identifier, denial code/message, product/service cost, and request type code and can determine if the pharmacy identified by the pharmacy identifier, the prescribed product (e.g., medication, device, etc.), service, or medication class identified by the prescribed product or service identifier, the reject type or basis for rejection, the product or service cost and/or the request type identified by the request type code.

The management module 142 may also electronically receive, process, and respond to requests from the EHR module 124 and/or the provider adherence module 128 of the healthcare provider computer 102, may electronically receive, process, and respond to requests of the network adherence module 144, may further electronically receive, process, and respond to requests of the benefits management module 160 of the pharmacy claims processor computer 106, and may further electronically receive, process, and respond to requests of the pharmacy management module 174 of the pharmacy computer 108. The service provider computer 104 may include additional program modules for performing other processing methods described herein. Those of ordinary skill in the art will appreciate that the service provider computer 104 may include alternate and/or additional components, hardware or software without departing from exemplary embodiments of the disclosure.

With continued reference to the service provider computer 104, the one or more I/O interfaces 134 may facilitate communication between the service provider computer 104 and one or more input/output devices, for example, one or more user interface devices, such as a display, keypad, keyboard, mouse, control panel, touch screen display, remote control, microphone, etc. that facilitate user interaction with the service provider computer 104. The one or more network interfaces 136 may facilitate connection of the service provider computer 104 to one or more suitable networks, for example, the network 110 illustrated in FIG. 1. In this regard, the service provider computer 104 may communicate with other components of the system 100.

One or more network adherence modules 144 may also be operative with or included with the service provider computer 104. The network adherence module 144 may include computer-executable instructions for facilitating the improved adherence monitoring system. In one example embodiment, the network adherence module 144 may be implemented as computer-implemented instructions of the memory 132 of the service provider computer 104.

Alternatively, the network adherence module 144 may also be implemented as computer-implemented instructions of a memory of a separate processor-based system communicably coupled to the service provider computer 104, according to another example embodiment.

The database 146 of FIG. 1 represents one or more databases that can be locally or remotely distributed with respect to the service provider computer 104 and/or the network adherence module 144. The database 146 may be operable to store information associated with various patients and/or from various prescription requests that have been electronically received by the service provider computer 104 and/or processed prescription request responses processed by the one or more pharmacy claims processor computers 106. The database 146 may also include, without limitation, one or more prescription benefit check files 176, one or more adherence files 178, and/or one or more vendor configuration files 180.

The one or more prescription benefit check files 176, may contain, without limitation, prescription information captured from one or more prescription benefit check requests, and/or one or more prescription request responses. For example, the one or more prescription benefit check files 176 may be include prescriber ID (e.g., a physician identification, a physician first/last name, etc.), medication identifier (e.g., a medication name, an NDC number, RX Norm, etc.), a quantity of medication to be dispensed, a number of refills available, and the like.

The one or more adherence files 178 may include, without limitation, information captured from a prescription fill notification request, a prescription fill notification response, and/or any other information communicated with relation to a patient adherence. For example, the one or more adherence files 178 may include, without limitation, a prescriber ID (e.g., a physician identification, a physician first/last name, etc.), medication identifier (e.g., a medication name, an NDC number, RX Norm, etc.), a service ID (e.g., pharmacy identification number, pharmacy name, pharmacy address, etc.), first fill request only, subsequent fill request, and the like.

The one or more vendor configuration files 180 may contain, without limitation, vendor information pertaining to adherence monitoring. More specifically, the one or more vendor configuration files 180 may include information indicating whether a prescription fill notification request should be generated for a designated prescription benefit check request communicated by the healthcare provider device 102 to the service provider computer 104 via the EHR vendor/aggregator 182.

With continued reference to FIG. 1, the pharmacy claims processor computer 106 (e.g., a pharmacy claims processor computer for a pharmacy claims processor) may be any suitable processor-driven device that facilitates receiving electronically, processing, and/or fulfilling healthcare claim requests, such as a prescription claim request, prescription billing request, or predetermination of benefits request, electronically received from the service provider computer 104. For example, the pharmacy claims processor computer 106 may be a processor-driven device associated with one or more PBMs, insurers, government payors, Medicare Part D payors, accountable care organizations, or claims clearinghouses. As desired, the pharmacy claims processor computer 106 may include any number of special purpose computers or other particular machines, application-specific circuits, microcontrollers, personal computers, minicomputers, mainframe computers, servers, and the like.

In certain exemplary embodiments, the operations of the pharmacy claims processor computer 106 may be controlled by computer-executed or computer-implemented instructions that are executed by one or more processors associated with the pharmacy claims processor computer 106 to form a special purpose computer or other particular machine that is operable to facilitate the receipt, processing, and/or fulfillment of prescription requests received from the service provider computer 104. The one or more processors that control the operations of the pharmacy claims processor computer 106 may be incorporated into the pharmacy claims processor computer 106 and/or in communication with the pharmacy claims processor computer 106 via one or more suitable networks. In certain embodiments, the operations and/or control of the pharmacy claims processor computer 106 may be distributed amongst several processing components.

Similar to other components of the system 100, the pharmacy claims processor computer 106 may include one or more processors 148, one or more memory devices 150, one or more input/output ("I/O") interfaces 152, and one or more network interfaces 154. The one or more memory devices 150 may be any suitable memory devices, for example, caches, read-only memory devices, random access memory devices, magnetic storage devices, removable memory devices. The one or more memory devices 150 may store data, executable instructions, and/or various program modules utilized by the pharmacy claims processor computer 106, for example, data files 156, an operating system ("OS") 158, and a benefits management module 160. The data files 156 may include any suitable information that is utilized by the pharmacy claims processor computer 106 to process prescription requests, for example, patient profiles, patient insurance information, other information associated with a patient, information associated with a healthcare provider, etc. The OS 158 may be a suitable software module that controls the general operation of the pharmacy claims processor computer 106. The OS 158 may also facilitate the execution of other software modules by the one or more processors 148, for example, the benefits management module 160. The OS 158 may be any currently existing or future-developed operating system including, but is not limited to, Microsoft Windows®, Apple OSX™, Linux, Unix, or a mainframe operating system.

The benefit management module 160 may be a suitable software module that facilitates access and management of one or more databases that are utilized to store information that is utilized by the pharmacy claims processor computer 106 in various example embodiments. The benefits management module may also initiate, receive, process, and/or respond to requests, such as prescription requests, from the management module 140 of the service provider computer 104. The pharmacy claims processor computer 106 may include additional program modules for performing other pre-processing or post-processing methods described herein. Those of ordinary skill in the art will appreciate that the pharmacy claims processor computer 106 may include alternate and/or additional components, hardware or software without departing from the example embodiments described herein.

The one or more I/O interfaces 152 may facilitate communication between the pharmacy claims processor computer 106 and one or more input/output devices, for example, one or more user interface devices, such as a display, keypad, keyboard, mouse, control panel, touch screen display, remote control, microphone, etc. that facilitate user interaction with the pharmacy claims processor computer 106. The one or more network interfaces 154 may facilitate connection of the pharmacy claims processor computer 106 to one or more suitable networks, for example, the network 110. In this regard, the pharmacy claims processor computer 106 may receive prescription requests and/or other communications from the service provider computer 104 and the pharmacy claims processor computer 106 may communicate information associated with processing the prescription requests and providing responses to the service provider computer 104.

With continued reference to FIG. 1, any number of pharmacy computers 108 may be associated with any number of pharmacies and/or pharmacists. Each pharmacy computer 108 may be any suitable processor-driven device that facilitates receiving electronically, processing, and/or fulfilling healthcare requests and/or prescription requests electronically received from the service provider computers 104. For example, a pharmacy computer 108 may be a processor-driven device associated with (i.e., located within) a pharmacy. As desired the pharmacy computer 108 may include any number of special-purpose computers or other particular machines, application-specific integrated circuits, microcontrollers, personal computers, minicomputers, mainframe computers, servers, and the like. In certain example embodiments, the operations of the pharmacy computer 108 may be controlled by computer-executed or computer-implemented instructions that are executed by one or more processors associated with the pharmacy computer 108 to form a special-purpose computer or other particular machine that is operable to facilitate the generation, processing, and/or fulfillment of prescription requests (e.g., a predetermination of benefits request, healthcare claim request, prescription claim request or prescription billing request) electronically transmitting t the service provider computer 104. The one or more processors that control the operations of a pharmacy computer 108 may be incorporated into the pharmacy computer 108 and/or may be in communication with the pharmacy computer 108 via one or more suitable networks. In certain example embodiments, the operations and/or control of the pharmacy computer 108 may be distributed among several processing components.

Similar to other components of the system 100, each pharmacy computer 108 may include one or more processors 162, one or more memory devices 164, one or more I/O interfaces 166, and one or more network interfaces 168. The one or more memory devices 164 may be any suitable memory devices, for example, caches, read-only memory devices, random access memory devices, magnetic storage devices, removable memory devices, etc. The one or more memory devices 164 may store data, executable instructions, and/or various program modules utilized by the pharmacy computer 108, for example, data files 170, an OS 172, and a pharmacy management module 174. The data files 170 may include any suitable information that is utilized by the pharmacy computer 108. The OS 172 may be a suitable software module that controls the general operation of the pharmacy computer 108. The OS 172 may also facilitate the execution of other software modules by the one or more processors 162. The OS 172 may be any currently existing or future-developed operating system including, but is not limited to, Microsoft Windows®, Apple OSX™, Linux, Unix, or a mainframe operating system.

The one or more I/O interfaces 166 may facilitate communication between the pharmacy computer 108 and one or more input/output devices, for example, one or more user interface devices, such as a display, keypad, control panel, touch screen display, remote control, microphone, etc., that facilitate user interaction with the pharmacy computer 108. The one or more suitable network interfaces 168 may facilitate connection of the pharmacy computer 108 to one or more suitable networks, for example, the network 110 illustrated in FIG. 1. In this require, the pharmacy computer 108 may electronically receive healthcare requests and/or communications from the service provider computer 104 and the pharmacy computer 108 may communicate information associated with processing healthcare requests to the service provider computer 104.

The pharmacy management module 174 may be a software application(s) including a dedicated program, for fulfilling healthcare request orders, reading and/or updating medical records (e.g., prescription records, facilitating patient billing, etc., as well as interacting with the service provider 104. For example, a pharmacist or other pharmacy employee, may utilize the pharmacy management module 174 in filling a prescription, recording and/or updating a patient's medical prescription history, billing a prescription, and preparing and providing a healthcare request for information to the service provider computer 104. Furthermore, the pharmacy computer 108 may utilize the pharmacy management module 174 to retrieve or otherwise electronically receive data, messages, or response from the healthcare provider device 102 and/or other components of the system 100.

With continued reference to FIG. 1, the system 100 may include any number of EHR vendor(s)/aggregator(s) 182. Each EHR vendor/aggregator 182 may be associated with any number of healthcare provider devices and computer systems 102 and may provide an electronic communications channel or pipeline between each respective healthcare provider device 102 and the service provider computer 104 via the network 110. In certain example embodiments, the EHR vendor/aggregator 182 provides a single-point access for the transmission of data and requests associated with or using a healthcare provider's electronic medical records system to the service provider computer 104 via the healthcare provider device 102. Furthermore, the EHR vendor/aggregator 182 may also provide access for the transmission of data and responses from the service provider computer 104 to the healthcare provider device 102. Each EHR vendor/aggregator 182 may also aggregate data received from multiple healthcare provider devices, pharmacy claims processor computers, and/or pharmacy computers for subsequent access by the healthcare provider device 102 and/or the service provider computer 104.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch requests to be electronically transmitted between or among the healthcare provider device 102, the service provider computer 104, the network adherence module 144, the database 146, the pharmacy claims processor computer 106, and/or the pharmacy computer 108. Due to network connectivity, various methodologies, as described herein may be practiced in the context of distributed computing environments. Although the service provider computer 104 is shown for simplicity as being in communication with the healthcare provider device 102, the network adherence module 144, the database 146, the pharmacy claims processor computer 106, and/or the pharmacy computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 104 may form the basis of network 110 that interconnects one or more of the healthcare provider device 102, the network adherence module 144, the database 146, the pharmacy claims processor computer 106, and the pharmacy computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 104 (or other computer) may be implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2A:
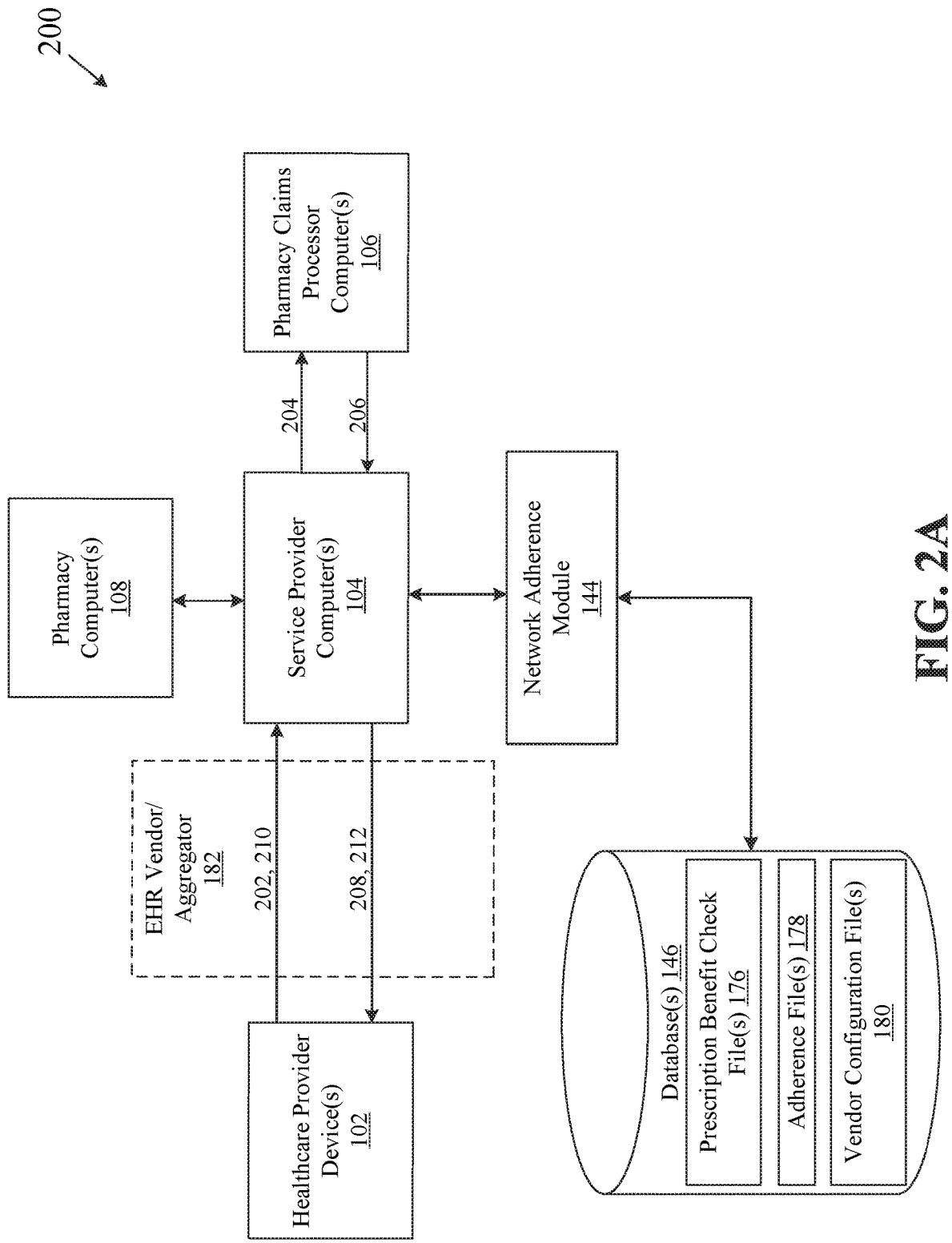
FIG. 2A is a diagram of an example system flow for providing improved adherence monitoring according to one exemplary embodiment.
Figure 3A:
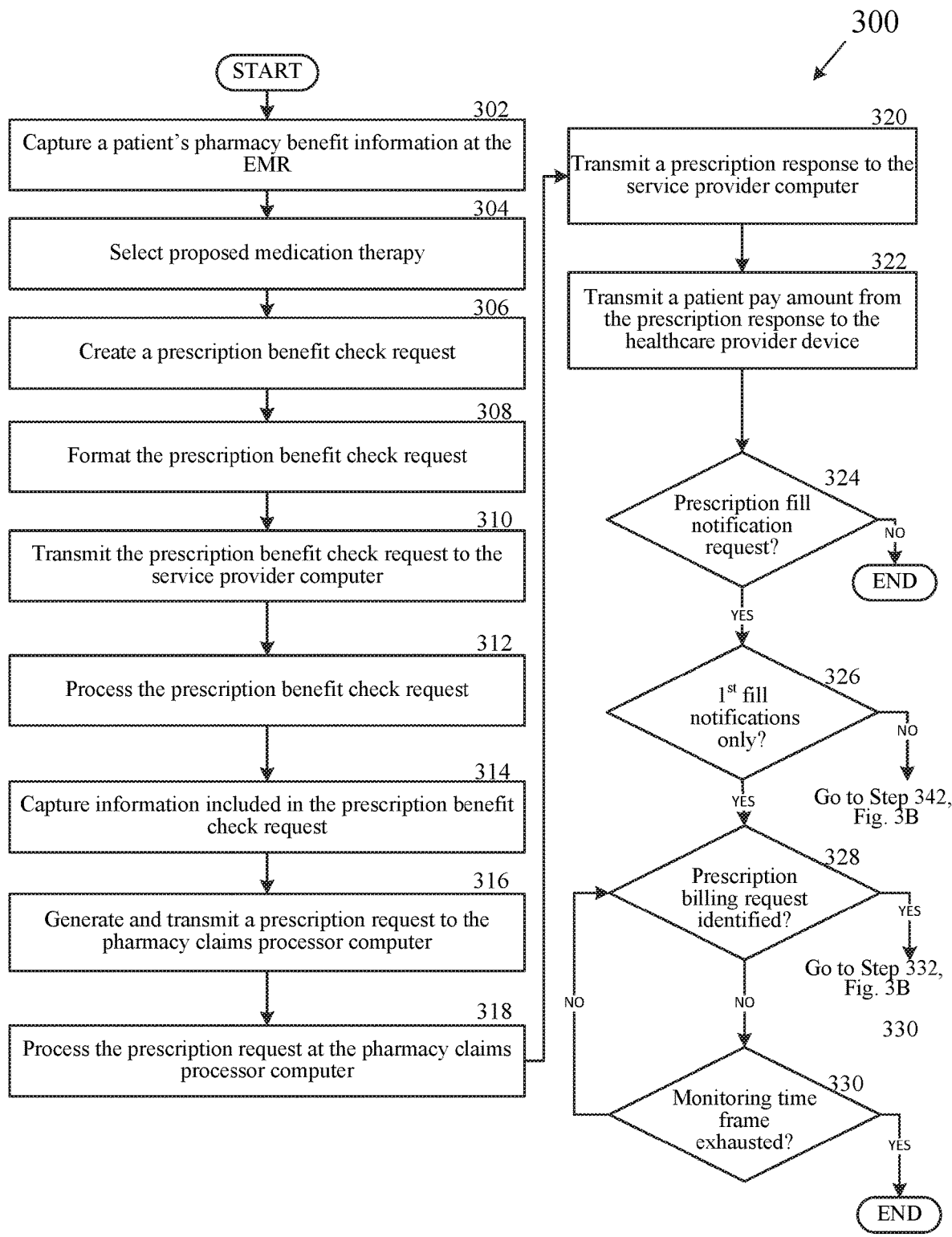
FIGS. 3A-3B are an exemplary methodology for implementing the improved adherence monitoring system, in accordance with one exemplary embodiment.
Figure 3B:
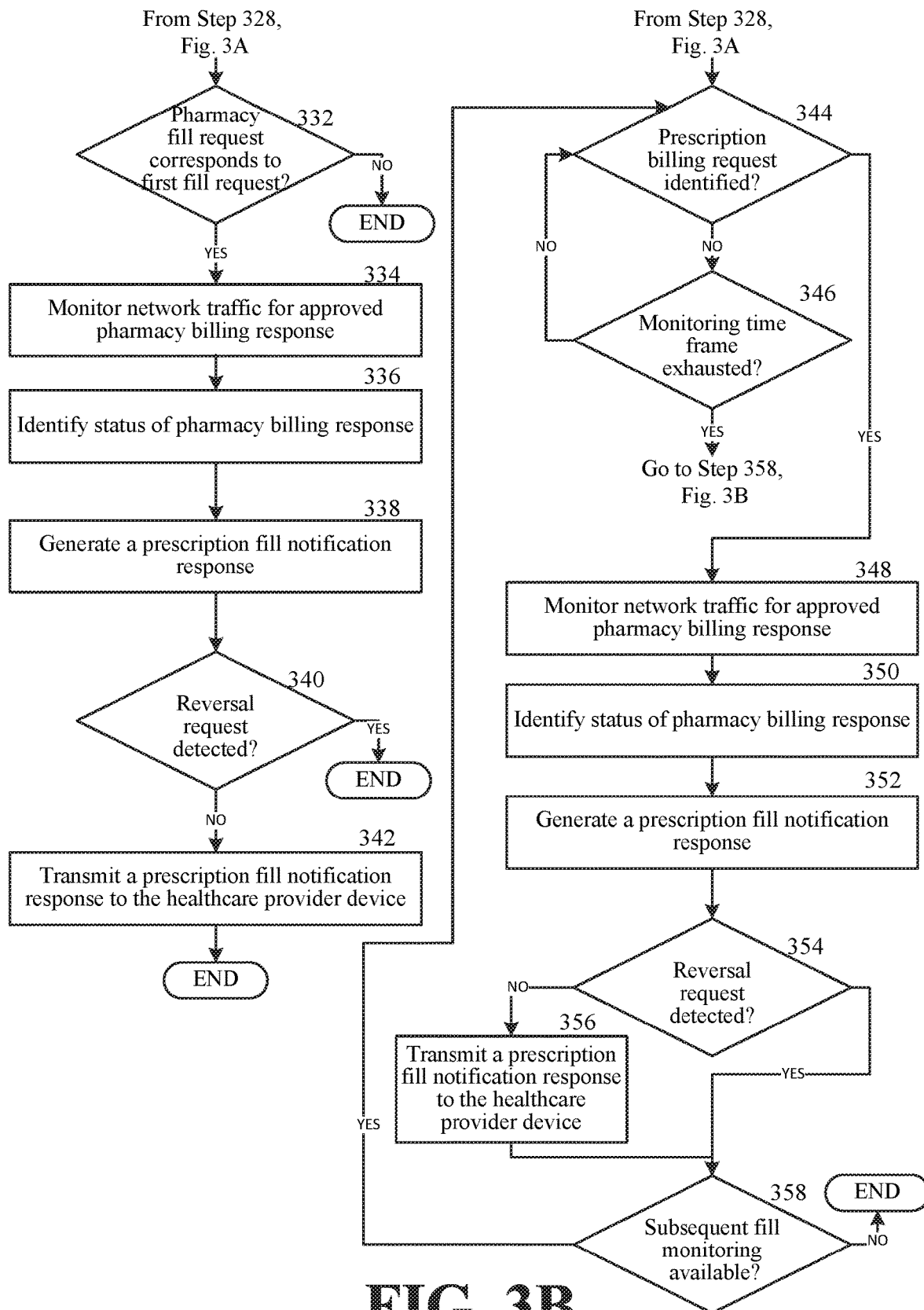

FIG. 2A is a diagram of one example data flow 200 for the improved adherence monitoring system as part of or in-line with the processing of a prescription benefit check request and a prescription request through a service provider, such as through the service provider computer 104 illustrated in FIG. 1. FIGS. 3A-3B are flow charts of an example method 300 for implementing the improved adherence monitoring system as part of the processing of the prescription benefit check request and prescription request, such as, a prescription claim request, a prescription billing request, or a predetermination of benefits request, in accordance with one exemplary embodiment. The exemplary method 300, described below, may be performed by a suitable service provider computer 104 and/or network adherence module 144.

The exemplary method 300 will be described with reference to a prescriber as the healthcare provider; however, this is only for purposes of example as other healthcare providers could be substituted for, and should each be individually read as being a part of each of these methods. As such, where the discussion of the methods below and the drawings state a physician, any other healthcare provider could be substituted, such as a physician, hospital, physician's office, clinic, prescriber of the medication, or healthcare center.

In addition, the exemplary method 300 described below will be described with reference to a prescription request as the healthcare claim request; however, this also is only for purposes of example as other prescription requests (which may include, for example, a prescription claim request, prescription billing request, or predetermination of benefits request) could be substituted for the prescription request and each form of prescription request should each individually be read as being used in the methods described below Referring now to FIGS. 1, 2A, and 3A-B, the exemplary method 300 begins at the START step and proceeds to step 302, where the healthcare provider device, such as the healthcare provider device 102, may optionally be utilized to capture a patient's pharmacy benefit information. In one example implementation, the healthcare provider device 102 may employ an electronic health records (EHR) module 124 to capture the patient's pharmacy benefit information. The patient's pharmacy benefit information may be captured as a part of patient visit. For example, the patient's pharmacy benefit information may be captured as a part of an administrative function at the point of a patient admission (e.g., a patient registration). Alternatively, the patient's pharmacy benefit information may be captured at a time other than the patient visit. For example, the patient may communicate pharmacy benefit information utilizing a web-based portal from any patient desired location. Generally, the patient pharmacy benefit information may be found on a patient's pharmacy benefit card (e.g., patient insurance card). For example, without limitation, the EHR module 124 may capture from a patient's pharmacy benefit card, a BIN number, a processor control number, an assigned cardholder ID, person code, relationship code, and/or a group ID. Additional patient information not generally included on the patient's pharmacy benefit card that may be captured by the EHR module 124 includes, without limitation a patient's date of birth and/or a patient gender code. While the step above describes the capture of the patient's pharmacy benefit information, all or a portion of this step is optional and may explicitly be excluded from the example method 300 in other example embodiments.

At step 304, a prescriber may select a proposed medication therapy. The proposed medication therapy may include a medication identifier (e.g., National Drug Code (NDC) identification, RxNorm medication identifiers, a medication name, and the like). At step 306, the healthcare provider device 102 creates a prescription benefit check request 202. The prescription benefit check request 202 may include, without limitation, the patient pharmacy benefit information, proposed medication therapy, patient information, as well as prescriber information. While the example embodiment describes including each of the patient information, patient pharmacy benefit information, proposed medication therapy, and prescriber information into the prescription benefit check request 202, each of these types of information may optionally not be included in the request 202 when it is created and transmitted to the service provider computer 104. In example embodiments where one or more of these types of information is not included in the prescription benefit check request 202, the service provider computer 104 can evaluate historical prescription requests and/or prescription responses for the patient to identify the particular type of information (e.g., patient pharmacy benefit information, patient preferred pharmacy, patient identification information, etc.).

In one example, the provider adherence module 128 may optionally gather one or more of the patient information, the patient pharmacy benefit information, the proposed medication therapy, and the prescriber information. Alternatively, one or more of the patient information, the patient pharmacy benefit information, the proposed medication therapy, and the prescriber information may be input into the prescription benefit check request 202 manually by the prescriber. In one example implementation, the prescription benefit check request 202 may include, without limitation, the medication identifier, a total number of medications selected by the prescriber, the BIN number, the processor control number, a service provider ID (e.g., a patient's pharmacy of choice), the cardholder ID, the group ID, the person code, the patient's date of birth, the patient's gender code, the patient's first and/or last name, a product service ID, a prescriber ID, and/or a prescriber last name.

At step 308, the healthcare provider device 102 may format the prescription benefit check request 202. In one example implementation, the healthcare provider device 102 may employ the provider adherence module 128 to format the prescription benefit check request 202. According to one example embodiment, the prescription benefit check request 202 may be formatted in accordance with a proprietary standard, although other standards, including, but not limited to the National Council for Prescription Drug Programs (NCPDP) Telecommunication standard, may be utilized as well.

As discussed above, the prescription benefit check request 202 may include a BIN Number, a BIN Number and PCN, and/or a BIN Number and Group ID for identifying a particular pharmacy claims processor computer (e.g., PBM, healthcare insurance company, Medicare or other government healthcare insurance payor, Medicare Part D provider, etc.), such as the pharmacy claims processor computer 106, as a destination for the prescription benefit check request 202. In addition, the prescription benefit check request 202 may also include information relating to the patient, payor, prescriber, healthcare provider, and/or the requested product (e.g., medication or device) or service. As an example, the prescription benefit check request 202 may include one or more of the following information:

Payor identifier—Payor ID/Routing Information
    BIN Number (i.e. Banking Identification Number), BIN Number and Processor Control Number (PCN) and/or BIN Number and Group ID, that designates a destination (e.g., the pharmacy claims processor computer 106) of the prescription benefit check request 202
    Patient Information
    Name (e.g. Patient Last Name, Patient First Name, etc.)
    Date of Birth of Patient
    Age of Patient
    Gender
    Patient Address (e.g. Street Address, Zip Code, etc.)
    Patient Contact Information (e.g. patient telephone number, email address, etc.)
    Patient Health Condition Information
    Patient ID or other identifier (e.g., Health Insurance Claim Number (HICN), social security number, etc.)
    Insurance/Coverage Information
    Cardholder Name (e.g. Cardholder First Name, Cardholder Last Name)
    Cardholder ID and/or other identifier (e.g. person code)
    Group ID and/or Group Information
    Prescriber Information
    Primary Care Provider ID or other identifier (e.g. NPI code)
    Primary Care Provider Name (e.g. Last Name, First Name)
    Prescriber ID or other identifier (e.g. NPI code, DEA number)
    Prescriber Name (e.g. Last Name, First Name)
    Prescriber Contact Information (e.g. Telephone Number)
    Pharmacy Information
    Pharmacy or other Healthcare Provider Information (e.g. store name, store address, chain identifier, etc.)
    Pharmacy or other Healthcare Provider ID (e.g. NPI code)
    Claim Information Medication, service, or product information—Product (medication or device) or service identifier (e.g. National Drug Code (NDC code), RxNorm code, etc.), product or service name, etc.

Prescription/Service Reference Number

Date Prescription Written

Quantity Dispensed

Days' Supply

Diagnosis/Condition (e.g., diagnosis code)

Pricing information for the drug/service/product (e.g. ingredient cost (e.g., in an Ingredient Cost field), dispensing fee (e.g., in a Dispensing Fee field), gross amount due (e.g., in a Gross Amount Due field), and Usual and Customary Charge amount (e.g., in a Usual and Customary Charge field))

Number of Refills Authorized

Fill Number (i.e., the current refill number for the prescription benefit check request 202)

One or more NCPDP Message Fields

One or more Drug Utilization (DUR) Codes

Date of Service.

The prescription benefit check request 202 can be used to determine if the pharmacy claims processor associated with the pharmacy claims processor computer 106 approves or rejects payment coverage for the prescribed product (e.g., medications, devices, etc.) or service being requested in the prescription benefit check request 202 and, if approved, the amount the pharmacy claims processor will cover (or pay) for the prescribed product (e.g., medication, device, etc.) or service being requested and how much the patient pay amount (the amount the patient is responsible to pay for) will be.

The healthcare provider device 102 electronically transmits the prescription benefit check request 202 to the service provider computer 104 via EHR vendor/aggregator 182 in step 310. At step 312 the service provider computer 104 may process the prescription benefit check request 202. For example, the service provider computer 104 can parse the electronically received prescription benefit check request 202 to determine a destination identifier or pharmacy benefit provider ID in the prescription benefit check request 202 (e.g., based on the Banking Identification Number (BIN Number), the BIN Number and Processor Control Number (PCN) or the BIN Number and Group ID in one or more fields of the prescription benefit check request 202).

Processing of the prescription benefit check request 202 may also include identifying the request type of the prescription benefit check request 202. For example, based upon the determination of the destination pharmacy claims processor computer 106, the system may determine the type and format of a prescription request to be generated by the service provider computer 104 in order to identify information for a response to the prescription benefit check request 202. Examples of the prescription request can include, but are not limited to a pharmacy billing request "B 1" or a predetermination of benefits request "D1", formatted under the NCPDP Telecom standard or a request type not supported by the system of FIG. 1.

At step 314, the service provider 104 may capture information included in the one or more fields of the prescription request 204. For example, without limitation, the network adherence module 144 or another portion of the service provider computer 104 may capture, without limitation, the prescription fill notification request, the medication identifier, a total number of medications selected by the prescriber, the BIN number, the processor control number, a service provider ID (e.g., a patient's pharmacy of choice), the cardholder ID, the group ID, the person code, the patient's date of birth, the patient's gender code, the patient's first and/or last name, a product service ID, a prescriber ID, and/or a prescriber last name. The information captured in the prescription request 204 may be stored in one or more prescription benefit check files 176 in the database 146 and or the data files 138.

The service provider computer 104 may generate a prescription request 204 and all or a portion of the information in the prescription benefit check request 202 may be inserted into the prescription request 204 by the network benefit check module 110. Alternatively, the network benefit check module 110 can reformat the prescription benefit check request 202 into one of several forms of prescription request 204 formatted in accordance with the NCPDP Telecom standard. The service provider computer 104 may then electronically transmit the prescription request 204 to the pharmacy claims processor computer 106 in step 316. For example, a prescription request 204 can be electronically transmitted from the service provider computer 104 to the pharmacy claims processor computer 106 via the network 110. The pharmacy claims processor computer 106 electronically receives and processes the prescription request in step 318 to determine if the patient has coverage, to determine to what extent the patient's coverage covers the requested product or service identified in the request 204, and to generate a prescription response 206 as to whether the request 204 is approved/paid or denied. Example responses in the prescription response 206 can include, but are not limited to, accepted, approved, paid, captured, denied (e.g., rejected), and denied (e.g., rejected) with request for additional information and resubmission. In certain exemplary embodiments, the responses can be input into a field of the prescription request 204 that is recognized by the service provider computer 104 and/or the healthcare provider computer 102. Typically, if the response for the request 204 is approved, the prescription response 206 provides the amount of the cost of the medication, product, or service that will be covered by the pharmacy claims processor 106 (the total amount paid, which is provided in the Total Amount Paid field of the prescription response 206), any amount applied to a patient deductible which is provided in the amount applied to periodic deductible field of the prescription response 206), the patient pay amount (which is provided in the Patient Pay Amount field of the prescription response 206), a pharmacy name field populated with a short pharmacy name corresponding to the submitted service provider ID on the prescription request 204, and/or a pharmacy street address populated with a pharmacy street address corresponding to the submitted service provider ID on the prescription request 204. On the other hand, if the response is a denial, the prescription response 206 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

In step 320, the pharmacy claims processor computer 106 electronically transmits the prescription response 206 to the service provider computer 104 via, for example, the network 110. At step 322, the service provider computer 104, via the EHR vendor/aggregator 182, may electronically transmit a prescription benefit check response 208 to the healthcare provider computer 102. In one implementation, the prescription benefit check response 208 may include, without limitation, the information included in the prescription benefit check request 202 and at least the patient pay amount provided in the Patient Pay Amount field of the prescription response 206.

At step 324, the service provider device 104 may determine whether a prescription fill notification request 210 has been received from the healthcare provider device 102. In one example implementation, the healthcare provider device 102 may electronically transmit the prescription fill notification request 210 via the EHR vendor/aggregator 182 to the service provider computer 104 in response to the patient pay amount provided in the prescription benefit check response 208. For example, upon receipt of the patient pay amount, the prescriber (e.g., user 126) may manually select an option for a prescription fill request within the EHR module 124. The selection of the prescription fill request may prompt a prescriber to input additional information prior to generating the prescription fill notification request 210. For example, a prescription fill request may prompt a prescriber to fill out one or more questions within a prescription fill request questionnaire. The one or more questions may include, without limitation, does the prescriber have patient consent to request prescription fill information, is the medication/product a maintenance medication/product, is the prescription fill request a first fill request, is there a time period desired to monitor for a prescription fill, etc. The prescription fill notification request 210 may also include a prescriber ID, a patient ID, or the like. The service provider computer 104 may store the data included in the prescription fill notification request 210 in one or more adherence files 178.

Alternatively, the EHR module 124 of the healthcare provider device 102 may be configured to automatically generate and electronically transmit the prescription fill notification request 210 following the transmission of every prescription benefit check request to the service provider computer 104. Alternatively and/or additionally, the EHR module 124 may be configured to automatically generate a prescription fill notification request for every prescription benefit check request including a prescription for a medication and/or product of a specific class (e.g., a schedule I drug). Alternatively and/or additionally, the EHR module 124 may be configured to automatically generate a prescription fill notification request based on a patient diagnosis (e.g., a high blood pressure diagnosis). Alternatively and/or additionally, the EHR module 124 may be configured to automatically generate a prescription fill notification request for a specific prescriber type (e.g., gynecologist, neurologist, etc.), prescriber location (e.g., state, city, county, etc.), and/or a prescriber's practice size (e.g., large clinic, small clinic, multi prescriber clinic, single prescriber clinic, etc.). By way of another example, the EHR module 124 may be further configured to indicate whether the prescription fill notification request is a first fill adherence request only, or if the prescription fill notification request is an adherence request corresponding to all prescriptions, initial fill as well as any and all refills associated with a prescription. If the service provider computer 104 determines that a prescription fill notification request 210 has been received from the healthcare provider device 102, the YES branch is followed to step 326. On the other hand, if the service provider computer 104 determines that a prescription fill notification request 210 has not been received from the healthcare provider device 102, the NO branch is followed and processing may end after step 324.

At step 326, the network adherence module 144 or another portion of the service provider 104 determines whether the prescription fill notification request 210 was a first fill notification request only, or was a subsequent fill request (e.g., a maintenance drug may prescribe have multiple refills available). In one implementation, the network adherence module 144 may determine the fill request status by accessing fill request information from the prescription fill notification request 210 stored in the one or more adherence files 178. Alternatively and/or additionally, the network adherence module 144 may access the fill request information directly from the prescription fill notification request 210. If the prescription fill notification request is a first fill notification only request, the YES branch is to step 328. On the other hand, if the prescription fill notification request is a multiple fill notification request, the NO branch is followed to step 344.

At step 328, the network adherence module 144 or another portion of the service provider computer 104 may determine whether a pharmacy computer, such as pharmacy computer 108, has sent a pharmacy billing request associated with the product and/or patient identified in the prescription benefit check request 202, the prescription request 204, the prescription response 206, and/or the prescription benefit check response 208. In one implementation, the pharmacy billing request may be identified based upon a matching algorithm utilizing, without limitation, a prescriber ID, patient ID, and/or service ID. For example, a prescriber ID (e.g., a prescriber identification number, a prescriber first/last name, etc.), a patient ID, and/or a service ID may be identified from the prescription benefit check request 202 the prescription request 204, the prescription response 206, and/or the prescription benefit check response 208. The network adherence module 144 may monitor the network, for example, network 110, for any combination of the prescriber ID, patient ID, and/or service ID. If a pharmacy billing request was not identified, the NO branch is followed and processing may continue at step 330. However, if a pharmacy billing request was identified, the YES branch is followed and processing may continue to step 334.

At step 330, the network adherence module 144 determines whether a monitoring window was defined in the prescription fill notification request 210. In one implementation, the monitoring window may correspond to a time period (e.g., 1 month, 3 months, 6 months, 12, months, etc.) associated with a request to monitor billing/request traffic on the network, such as network 110. For example, the network may be monitored for activity associated with the prescription benefit check request 202, the prescription request 204, the prescription response 206, and/or the prescription benefit check response 208. If the monitoring window has expired, the prescription fill notification request 210 may be considered to have been exhausted and the network adherence module 144 will no longer monitor network traffic for billing/request information associated with the prescription benefit check request 202, the prescription request 204, the prescription response 206, and/or the prescription benefit check response 208. In one implementation, the monitoring window may be based upon the date the prescription benefit check request was submitted by the healthcare provider computer 102. Alternatively, the monitoring window may commence upon the receipt of the prescription fill notification request 210. If no monitoring window was defined, or the monitoring window has expired, the NO branch is followed and the process may end after step 330. However, if a monitoring window was, and/or the monitoring window has not expired, the YES branch is followed and processing may return to step 328.

At step 332, the network adherence module 144 determines whether the identified pharmacy billing request corresponds to a first fill request or a subsequent fill request. In one implementation, the determination may be based upon information included in the identified pharmacy billing request. For example, if the pharmacy billing request is a B1 request formatted under the NCPDP Telecom standard, the network adherence module 144 may utilize the NCPDP Field Number 403-D3 (e.g., the field would be populated with a "0") to determine if the request is a first fill request. If the identified pharmacy billing request corresponds to a first fill, the YES branch is followed to step 334. If however, the identified pharmacy billing request corresponds to a subsequent fill, the NO branch and the process may end after step 332

At step 334, the network adherence module 144 monitors traffic over the network (for example network 110) to determine whether a pharmacy response has been issued by the pharmacy claims processor computer 106 for the identified pharmacy billing request. In one implementation, the pharmacy billing response 210 may be identified based upon a matching algorithm utilizing, without limitation, a prescriber ID, patient ID, and/or service ID. If a pharmacy billing response was identified, the YES branch is followed and processing may continue to step 336. However, if a pharmacy billing response was not identified, the NO branch is followed and processing may end after step 334.

At step 336, the network adherence module 144 identifies a status of the pharmacy billing response as an approved/paid status or as a denied/unpaid status. In one example implementation, the status may be identified based upon a status indicator in field in the pharmacy billing response. In one implementation, a pharmacy billing response that retains an approved (e.g., paid) status, is determined to be a "filled" prescription.

At step 338, the network adherence module 144 or another portion of the service provider computer 104 may generate a prescription fill notification response 212. In one example implementation, the prescription fill notification response may include information (e.g., patient information, prescriber information, fill information, etc.) similar to the prescription fill notification request 210. At step 340, the network adherence module 144 determines whether a reversal request corresponding to the pharmacy billing request and/or pharmacy billing response has been identified. In one implementation, the network adherence module 144 may determine whether a reversal request has been identified by, at least, monitoring the network (e.g., network 110). In one example implementation, the network adherence module 144 may monitors the network for a period of about 14 days following the identification of the pharmacy billing response. While the monitoring period is described to be 14 days, it is to be appreciated that any monitoring period is configurable. If no reversal request is identified, the prescription fill notification response 212 is generated and the NO branch is followed to step 342. On the other hand, if a reversal request is identified, the YES branch is followed and the process may end after step 340.

At step 342, the prescription fill notification response 212 is electronically communicated to the healthcare provider device 102. In one implementation, the prescription fill notification response 212 may include an indication that the medication/product was filled by the pharmacy (e.g., the pharmacy computer 108). A "filled" prescription by a pharmacy may equate to a patient picking up the prescription, and therefore, patient adherence with regards to the prescribed medication/product. The process may end after step 340.

A prescription fill notification request 210 that includes a request for notification with respect to multiple fills (see step 328) continues at step 344. At step 344, the network adherence module 144 or another portion of the service provider computer 104 monitors the network to determine whether a pharmacy computer, such as pharmacy computer 108, has sent a pharmacy billing request associated with the product and/or patient identified in the prescription benefit check request 202, the prescription request 204, the prescription response 206, and/or the prescription benefit check response 208. In one implementation, the pharmacy billing request may be identified based upon a matching algorithm utilizing, without limitation, a prescriber ID, patient ID, and/or service ID. For example, a prescriber ID (e.g., a prescriber identification number, a prescriber first/last name, etc.), a patient ID, patient gender, patient date of birth, patient gender, and/or a service ID may be identified from the prescription benefit check request 202 the prescription request 204, the prescription response 206, and/or the prescription benefit check response 208. If a pharmacy billing request was not identified, the NO branch is followed and processing may continue at step 346. However, if a pharmacy billing request was identified, the YES branch is followed and processing may continue to step 348.

At step 346, the network adherence module 144 determines whether a monitoring window was defined in the prescription fill notification request 206. In one implementation, the monitoring window may correspond to a time period (e.g., 1 month, 3 months, 6 months, 12, months, etc.) associated with a request to monitor billing/request traffic on the network, such as network 110. For example, the network may be monitored for activity associated with the prescription benefit check request 202, the prescription request 204, the prescription response 206, and/or the prescription benefit check response 208. If the monitoring window has expired, the prescription fill notification request 210 may be considered to have been exhausted and the network adherence module 144 will no longer monitor network traffic for billing/request information associated with the prescription benefit check request 202, the prescription request 204, the prescription response 206, and/or the prescription benefit check response 208. In one implementation, the monitoring window may be based upon the date the prescription benefit check request was submitted by the healthcare provider computer 102. Alternatively, the monitoring window may commence upon the receipt of the prescription fill notification request 210. If no monitoring window was defined, or the monitoring window has expired, the NO branch is followed and the process may continue to step 358. However, if a monitoring window was defined, and/or the window has not been expired, the YES branch is followed and processing may return to step 346.

At step 348, the network adherence module 144 the network adherence module 144 monitors traffic over the network (for example network 110) to determine whether a pharmacy response has been issued by the pharmacy claims processor computer 106 for the identified pharmacy billing request. In one implementation, the pharmacy billing response 210 may be identified based upon a matching algorithm utilizing, without limitation, a prescriber ID, patient ID, and/or service ID. However, if a pharmacy billing response was identified, the YES branch is followed and processing may continue to step 350. If a pharmacy billing response was not identified, the NO branch is followed and processing may continue to step 358.

At step 350, the network adherence module 144 identifies a status of the pharmacy billing response as an approved/ paid status or as a denied/unpaid status. In one example implementation, the status may be identified based upon a status indicator in field in the pharmacy billing response. In one implementation, a pharmacy billing response that retains an approved (e.g., paid) status, is determined to be a "filled" prescription.

At step 352, the network adherence module 144 or another portion of the service provider computer 104 may generate a prescription fill notification response 212. In one example implementation, the prescription fill notification response may include information (e.g., patient information, prescriber information, fill information, etc.) similar to the prescription fill notification request 210. At step 354, the network adherence module 144 determines whether a reversal request corresponding to the pharmacy billing request and/or pharmacy billing response has been identified. In one implementation, the network adherence module 144 may determine whether a reversal request has been identified by, at least, monitoring the network (e.g., network 110). In one example implementation, the network adherence module 144 may monitors the network for a period of about 14 days following the identification of the pharmacy billing response. While the monitoring period is described to be 14 days, it is to be appreciated that any monitoring period is configurable. If no reversal request is identified, the prescription fill notification response 210 is generated and the NO branch is to step 356. On the other hand, if a reversal request is identified, the YES branch is followed and the process may continue at step 358.

At step 356, the prescription fill notification response 210 is electronically communicated to the healthcare provider device 102 via the EHR vendor/aggregator 182. In one implementation, the prescription fill notification response 212 may include an indication that the medication/product was filled the pharmacy (e.g., the pharmacy computer 108). A "filled" prescription by a pharmacy may equate to a patient picking up the prescription, and therefore, patient adherence with regards to the prescribed medication/product.

At step 358, service provider computer 104 determines whether subsequent fill monitoring is available for the prescription benefit check request 202. In one implementation, the prescription benefit check request 202 may include, without limitation, a one or more subsequent fill monitoring criteria. For example, the one or more subsequent fill monitoring criteria may include, without limitation, a request to monitor for one or more fills during a specified time period (e.g., a 12 month period, or any suitable time period), a request to monitor for a total number of fills (e.g., 3 fills, 5 fills, or any suitable number), a request to monitor for one or more fills until a refill status for the corresponding medication/product has been exhausted (e.g., the matching algorithm described herein could utilize the NCPDP Field Number 415-DF to determine the actual number of refills authorized), and/or any combination thereof. If subsequent fill monitoring is available, the process may return to step 344. If however, subsequent fill monitoring is not available, the process may end after step 358.

While the process is described to end after step 356, it is to be appreciated that a prescriber (e.g., user 126) may opt to cancel tracking of subsequent fill(s) notifications for a selected patient and/or for a particular NDC. To cancel the tracking of subsequent fills, the prescriber may utilize the EHR module 124 to generate a cancelation request, and communicate that cancellation request to the service provider computer 104.

Figure 4:
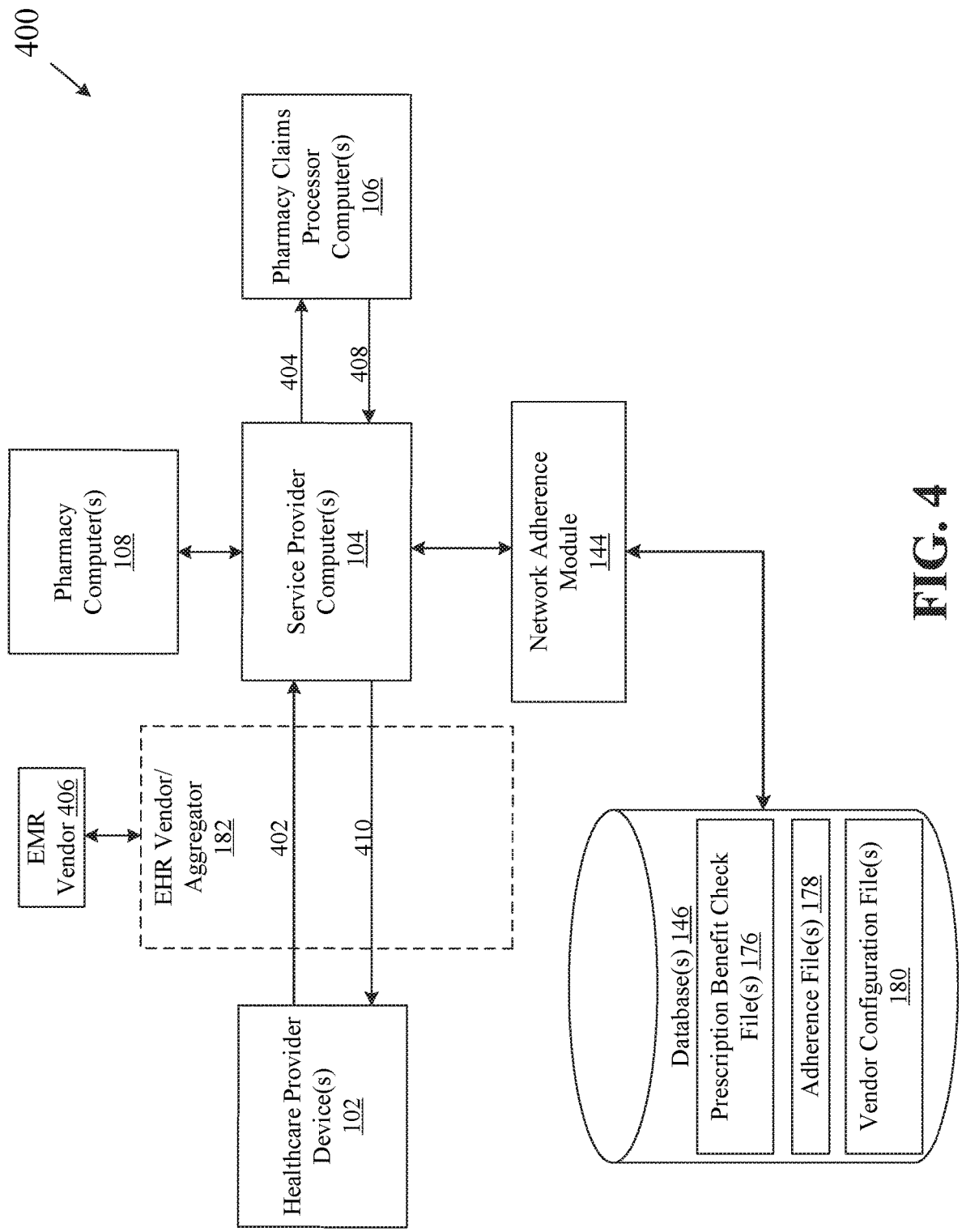
FIG. 4 is a diagram of another example system flow for providing improved adherence monitoring according to one exemplary embodiment.
Figure 5:
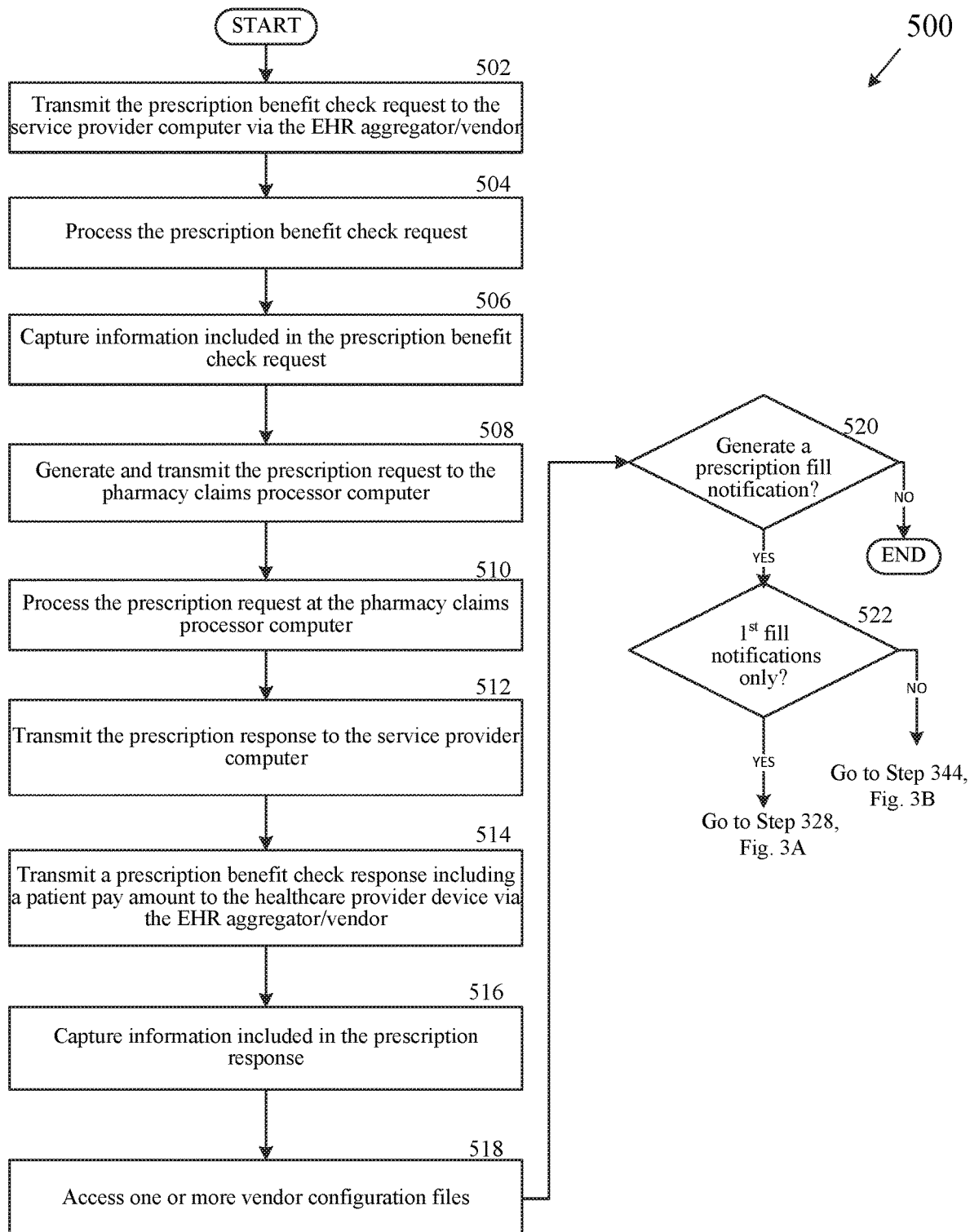
FIG. 5 is an exemplary methodology for implementing another improved adherence monitoring system, in accordance with one exemplary embodiment.

FIG. 4 is a diagram of one example data flow 400 for another improved adherence monitoring system as part of or in-line with the processing of a prescription request through a service provider via an EHR vendor/aggregator 182, such as through the service provider computer 104 illustrated in FIG. 1. FIG. 5 is a flow chart of an example method 500 for implementing the improved adherence monitoring system as part of the processing of the prescription request, such as a prescription benefit check request, prescription claim request, prescription billing request, or predetermination of benefits request, in accordance with one exemplary embodiment. The exemplary method 500, described below, may be performed by a suitable service provider computer 104 and/or network adherence module 144.

Similar to method 300, the exemplary method 500 will be described with reference to a prescriber as the healthcare provider; however, this is only for purposes of example as other healthcare providers could be substituted for, and should each be individually read as being a part of each of these methods. As such, where the discussion of the methods below and the drawings state a physician, any other healthcare provider could be substituted, such as a hospital, physician's office, clinic, prescriber of the medication, or healthcare center.

In addition, the exemplary method 500 described below will be described with reference to a prescription request as the healthcare claim request; however, this also is only for purposes of example as other prescription requests (which may include, for example, a prescription claim request, prescription billing request, or predetermination of benefits request) could be substituted for the prescription request and each form of prescription request should each individually be read as being used in the methods described below Referring now to FIGS. 1, 2A, 3A, 3B, 4, and 5 the exemplary method 500 begins at the START step and proceeds to step 502, where the healthcare provider device, such as the healthcare provider device 102, electronically transmits a prescription benefit check request 402 to the service provider computer 104 via the EHR vendor/aggregator 182. In one implementation, the prescription benefit check request 402 is generated in a similar fashion to the generation of prescription benefit check request 202 described with reference to FIGS. 3A and 3B. At step 504, the service provider computer 104 may process the prescription benefit check request 402. For example, the service provider computer 104 can parse the electronically received prescription benefit check request 402 to determine a destination identifier or pharmacy benefit provider ID (e.g., based on the Banking Identification Number (BIN Number), the BIN Number and Processor Control Number (PCN) or the BIN Number and Group ID in one or more fields of the prescription benefit check request 402). Processing of the prescription benefit check request 402 may also include identifying a request type. For example, based upon the determination of the destination pharmacy claims processor computer 106, a prescription request 404 may be determined to be a pharmacy billing request "B1" or a predetermination of benefits request "D1" formatted under the NCPDP Telecom standard, or a request type not supported by the system of FIG. 1.

Processing of the prescription benefit check request 402 may further include an identification of a vendor associated with the EHR vendor/aggregator 182. For example, the EHR vendor/aggregator 182 may be associated with a particular EMR vendor 406. The EHR vendor/aggregator 182 may represent a dedicated communication pathway by which an EHR module on a healthcare provider device (e.g., EHR 124 of healthcare provider device 102) communicates with a service provider computer, such as service provider computer 104. In one implementation, one or more prescribers (e.g., user 126 of healthcare provider device 102) may be qualified by a single EHR vendor 406. The EHR vendor 406 may provide a healthcare provider device (e.g., healthcare provider device 102) access to an EHR system (e.g., EHR 124) that may be used by a prescriber to perform a multitude of tasks, such as, the generation of a prescription benefit check request. Each EHR vendor may have an established communication pathway (e.g., EHR vendor/aggregator 182) by which the EHR communicates with the service provider computer 104. Therefore, every prescriber utilizing an EHR system associated with a particular EHR vendor will communicate with the service provider computer 104 via the same EHR vendor/aggregator 182.

At step 506, the service provider 104 may capture information included in the one or more fields of the prescription benefit check request 402. For example, without limitation, the network adherence module 144 or another portion of the service provider computer 104 may capture, without limitation, the medication identifier, a total number of medications selected by the prescriber, the BIN number, the processor control number, a service provider ID (e.g., a patient's pharmacy of choice), the cardholder ID, the group ID, the person code, the patient's date of birth, the patient's gender code, the patient's first and/or last name, a product service ID, a prescriber ID, and/or a prescriber last name. The information captured in the prescription benefit check request 202 may be stored in one or more prescription benefit check files 176 accessed in the database 146 and or the data files 138.

The service provider computer 104 may generate a prescription request 404 and all or a portion of the information in the prescription benefit check request 402 may be inserted into the prescription request 404 by the network benefit check module 110. Alternatively, the network benefit check module 110 can reformat the prescription benefit check request 402 into one of several forms of prescription request 404 formatted in accordance with the NCPDP Telecom standard. The service provider computer 104 may then electronically transmit the prescription request 404 to the pharmacy claims processor computer 106 in step 508. For example, a prescription request 404 can be electronically transmitted from the service provider computer 104 to the pharmacy claims processor computer 106 via the network 110. The pharmacy claims processor computer 106 electronically receives and processes the prescription request 404 in step 510 to determine if the patient has coverage, to determine to what extent the patient's coverage covers the requested product or service identified in the request 404, and to generate a prescription response 408 as to whether the request 404 is approved/paid or denied. Example request responses in the prescription response 408 can include, but are not limited to, accepted, approved, paid, captured, denied (e.g., rejected), and denied (e.g., rejected) with request for additional information and resubmission. In certain exemplary embodiments, the responses can be input into a field of the prescription request 404 that is recognized by the service provider computer 104 and/or the healthcare provider computer 102. Typically, if the response for the request 404 is approved, the prescription response 408 provides the amount of the cost of the medication, product, or service that will be covered by the pharmacy claims processor 106 (the total amount paid, which is provided in the Total Amount Paid field of the prescription response 408), any amount applied to a patient deductible which is provided in the amount applied to periodic deductible field of the prescription response 408), the patient pay amount (which is provided in the Patient Pay Amount field of the prescription response 408), a pharmacy name field populated with a short pharmacy name corresponding to the submitted service provider ID on the prescription request 404, and/or a pharmacy street address populated with a pharmacy street address corresponding to the submitted service provider ID on the prescription request 404. On the other hand, if the response is a denial, the prescription benefit check response 408 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

In step 512, the pharmacy claims processor computer 106 electronically transmits the prescription response 408 to the service provider computer 104 via, for example, the network 110. At step 514, the service provider computer 104, via the EHR vendor/aggregator 182, may electronically transmit a prescription benefit check response 410 to the healthcare provider computer 102. In one implementation, the prescription benefit check response 410 may include, without limitation, the information included in the prescription benefit check request 402 and at least the patient pay amount provided in the Patient Pay Amount field of the prescription response 408.

At step 516, the service provider computer 104 may capture information included in the one or more fields of the prescription response 408. For example, without limitation, the network adherence module 144 or another portion of the service provider computer 104 may capture fields from the prescription benefit check response 304 such as the request indicator status (e.g., a paid response or "P"), identification of the request response type (e.g., a prescriber billing request or a predetermination of benefits requests), a pharmacy name field populated with a short pharmacy name corresponding to the submitted service provider ID on the prescription benefit check request 402, and/or a pharmacy street address populated with a pharmacy street address corresponding to the submitted service provider ID, a prescriber ID, and/or patient identification (e.g., patient's birthdate, patient's first and/or last name, or the like). The information captured in the prescription response 408 may be stored in one or more prescription benefit check files 176 stored in the database 146 and or the data files 138.

At step 518, the network adherence module 144 or another portion of the service provider computer 104 may access one or more vendor configuration files 180 associated with the EHR vendor/aggregator 182 and/or the associated EHR vendor 406. At step 520, the network adherence module 144 or another portion of the service provider computer 104 may utilize the accessed or more vendor configuration files 180 to determine whether a prescription fill notification request should be generated for the corresponding prescription response 408. For example, for a particular prescriber (e.g., user 126), an EHR vendor 406 may specify in the one or more vendor configuration files the automatic generation of a prescription fill notification request for all prescription requests communicated via the EHR vendor/aggregator 182. Alternatively and/or additionally, the EHR vendor may specify a prescription fill notification request for every prescription request including a prescription for a medication and/or product of a specific class (e.g., a schedule I drug) for every qualified prescriber or a specified qualified prescriber. Alternatively and/or additionally, the EHR vendor may request the generation of a prescription fill notification based on a patient diagnosis (e.g., a high blood pressure diagnosis) for every qualified prescriber or for a specific qualified prescriber. Alternatively and/or additionally, a prescription fill notification request may be specified for a specific prescriber type (e.g., gynecologist, neurologist, etc.), prescriber location (e.g., state, city, county, etc.), and/or a prescriber's practice size (e.g., large clinic, small clinic, multi prescriber clinic, single prescriber clinic, etc.). By way of another example, an EHR vendor may further specify whether the prescription fill notification request is a first fill adherence request only, or if the prescription fill notification request is an adherence request corresponding to all prescriptions, initial fill as well as any and all refills. If a prescription fill notification request exists in the one or more vendor configuration files for the identified prescriber, the YES branch is followed to step 522. If however, the one or more configuration files for the identified prescriber do not include a prescription fill notification request, the NO branch is followed and processing may end following step 520.

At step 522, the network adherence module 144 or another portion of the service provider 104 determines whether the prescription fill notification request was a first fill notification request only. In one implementation, the network adherence module 144 may access the identified one or more vendor configuration files to determine whether the prescriptions fill notification request was a first fill notification request only. If the prescription fill notification request is a first fill notification only request, the YES branch is to step 328 of FIG. 3A. On the other hand, if the prescription fill notification request is a multiple fill notification request, the NO branch is followed to step 344 of FIG. 3B.

Figure 6:
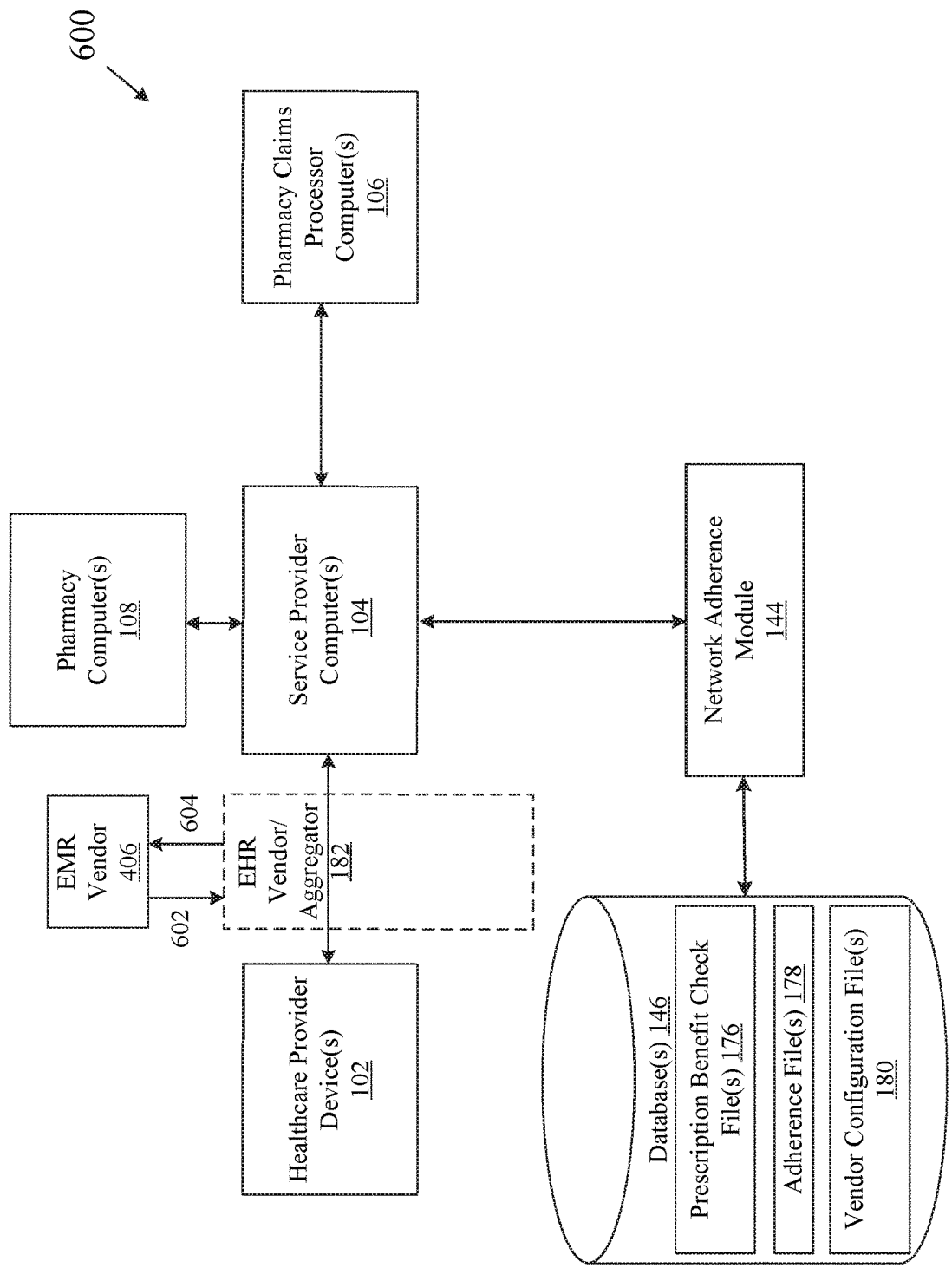
FIG. 6 is a diagram of another example system flow for providing reporting of adherence monitoring according to one exemplary embodiment.
Figure 7:
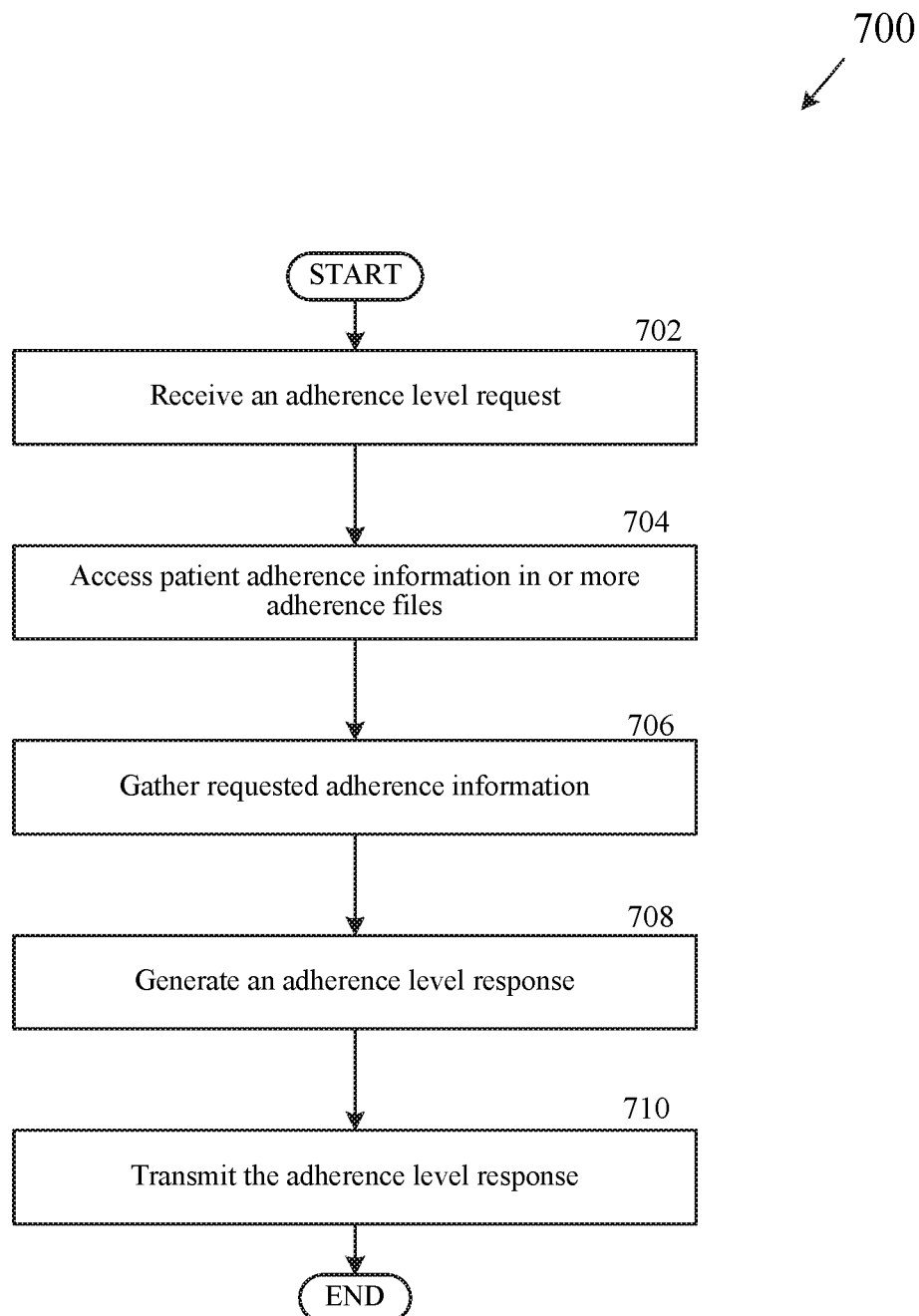
FIG. 7 is an exemplary methodology for implementing reporting of adherence monitoring, in accordance with one exemplary embodiment.'

FIG. 6 is a diagram of one example data flow 600 for another improved adherence monitoring system as part of or in-line with the processing of an adherence request through a service provider, such as through the service provider computer 104 illustrated in FIG. 1. FIG. 7 is a flow chart of an example method 700 for implementing another improved adherence monitoring system as part of the processing of the adherence request, such as a prescription fill rate, in accordance with one exemplary embodiment. The exemplary method 700, described below, may be performed by a suitable service provider computer 104 and/or network adherence module 144.

Referring now to FIGS. 1, 2A, 3A, 3B, 4, 5, 6, and 7 the exemplary method 700 begins at the START step and proceeds to step 702, where the service provider computer, such as the service provider computer 104, may electronically receive an adherence level request 602 over a network, such as network 110 via the EHR vendor/aggregator 182. The adherence level request 602 may be electronically received from an EHR vendor 406. Alternatively and/or additionally, an adherence level request 602 may be received from a healthcare provider device 102, a pharmacy claims processor computer 106, and/or pharmacy computer 108. In one implementation, the adherence level request 602 may include, without limitation, request for information corresponding to a particular prescriber, information corresponding to a particular patient, information corresponding to a fill rate for all patients associated with a particular prescriber, information corresponding to a fill rate for a therapeutic drug class, information based upon patient pay amount (e.g., patient co-pay), and the like. Alternatively and/or additionally, the adherence level request 602 may include, without limitation, an adherence level request from an EHR standpoint. For example, an adherence level request for a prescriber base as a whole. The adherence level request 602 may further include one or more search parameters. For example, the adherence level request 602 may include a prescriber ID (e.g., a prescriber identification, a prescriber first/last name, a prescriber location (e.g., physical address, state, region, and the like), a search time frame (e.g., last 30 days, last 6 months, all of 2015, from 2012-2015, etc.).

At step 704, the service provider computer 104 may access patient adherence information. In one example implementation, the service provider computer 104 may employ the network adherence module 144 to access one or more adherence files 178. As described herein, the one or more adherence files 178 may include, without limitation, information captured from a prescription fill notification request, a prescription refill notification request, a prescription fill notification response, and/or a prescription refill notification response.

At step 706, the network adherence module 144 may utilize the one or more search parameters included in the adherence level request 602 to gather the requested adherence information. For example, if the adherence level request 602 included a prescriber name John Smith and a search time period for the last 30 days, the network adherence module 144 may collect all of the information in the one or more adherence files 178 pertaining to Dr. John Smith for the last 30 days.

At step 708, the service provider computer 104 may generate an adherence level response 604 including all of the information collected. At step 710, the adherence level response 604 may be electronically communicated to the EHR vendor 406 for distribution to the healthcare provider computer, the claims processor computer, or the pharmacy computer via the EMR vendor/aggregator 182. The process may end after step 710.

Figure 8:
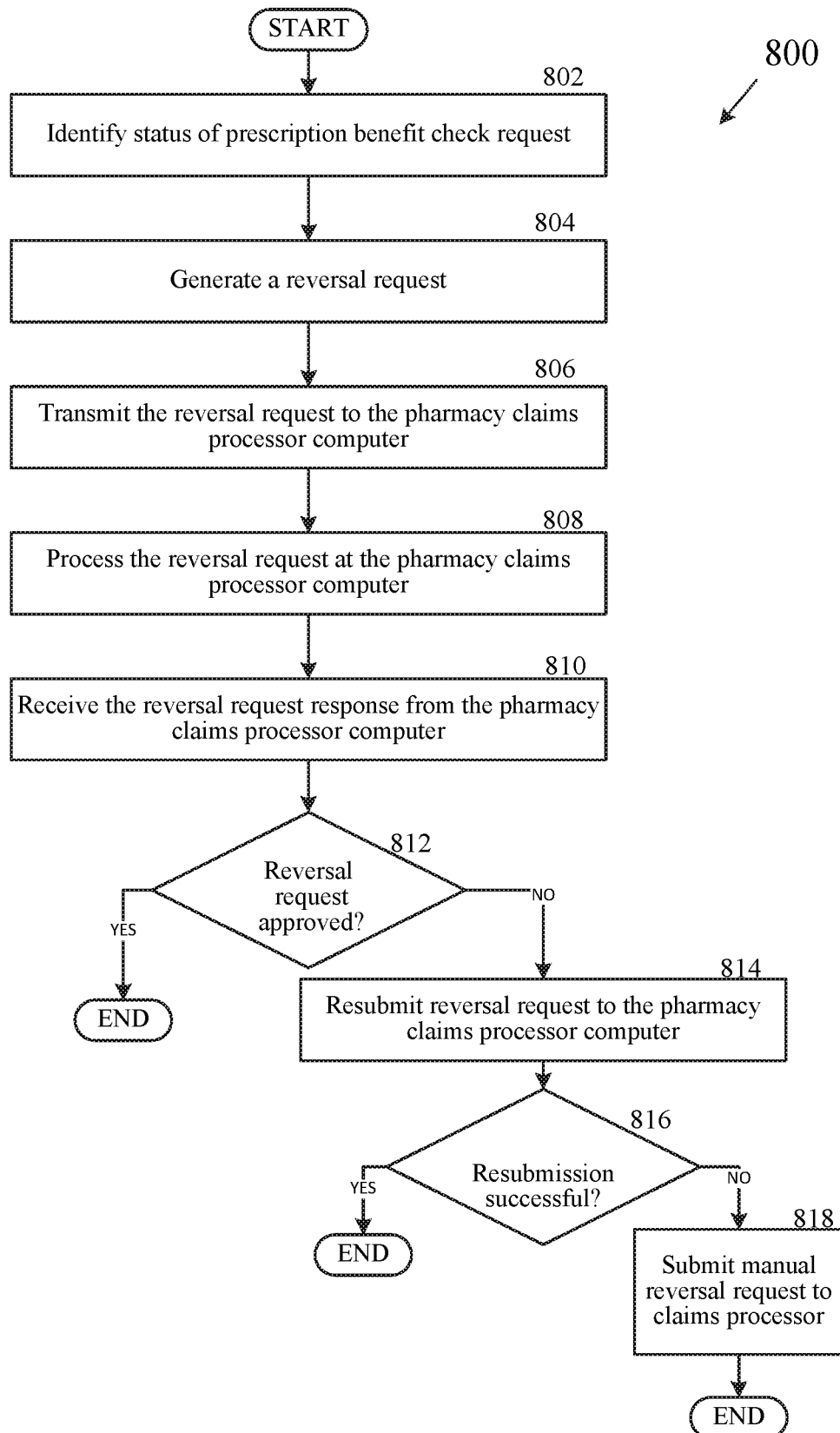
FIG. 8 is an exemplary methodology for providing improved adherence monitoring according to one exemplary embodiment.

FIG. 8 illustrates an example method 800 for receiving electronically and communicating a reversal request, according to the example embodiment of the disclosure.

Referring now to FIGS. 1A, 1B, 2A, 3A-B, 5, the exemplary method 800 begins at the START step and continues to step 802, where the service provider computer 104 may identify where the prescription benefit check request 202 was paid. In one non-limiting example, the service provider computer 104 may determine whether the prescription benefit check 202 was paid by identifying the request status indicator field in the prescription benefit check response 204. If the request status indicator field is populate a "P", and then the request was paid. If the request status indicator field is populated with an "R", then the request was rejected.

At step 804, the service provider computer 104 may generate a reversal request based at least in part upon the corresponding billing request type (e.g. B1 or D1) and the corresponding defined format described herein.

At step 806, the service provider computer 104 may electronically transmit the reversal request to the pharmacy claim processor computer 106. In one implementation, the pharmacy claims processor computer 106 is the same benefits computer that the prescription benefit check request 202 was previously submitted to. At step 808, the pharmacy claims processor computer 106 may process the reversal request. At step 810, the service provider computer 104 may electronically receive the reversal request response from the pharmacy claims processor computer 106.

At step 812, the service provider computer 104 may determine whether the reversal request was approved. If the reversal request was approved, the YES branch is followed and the process may end after step 812. If the reversal request was not approved, the NO branch is followed and processing may continue to step 814.

At step 814, the service provider computer 104 may resubmit the reversal request to the pharmacy claims processor computer 106. The reversal request may be resubmitted to the pharmacy claims processor computer 106 for a predetermined number of attempts. At step 816, the service provider computer 104 may determine whether the resubmission of the reversal request was successful. If the resubmission of the reversal request was approved, the YES branch is followed and the process may end after step 816. If the resubmission of the reversal request was not approved, then NO branch is followed and processing may proceed to step 818.

At step 818, the service provider computer 104 may submit a manual reversal request to pharmacy claims processor computer 106. The method 800 may end after step 818.

The methods described and shown in FIGS. 3A-B, 5, 7, and 8 may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3A-B, 5, 7, and 8 may be performed.

Figure 2B:
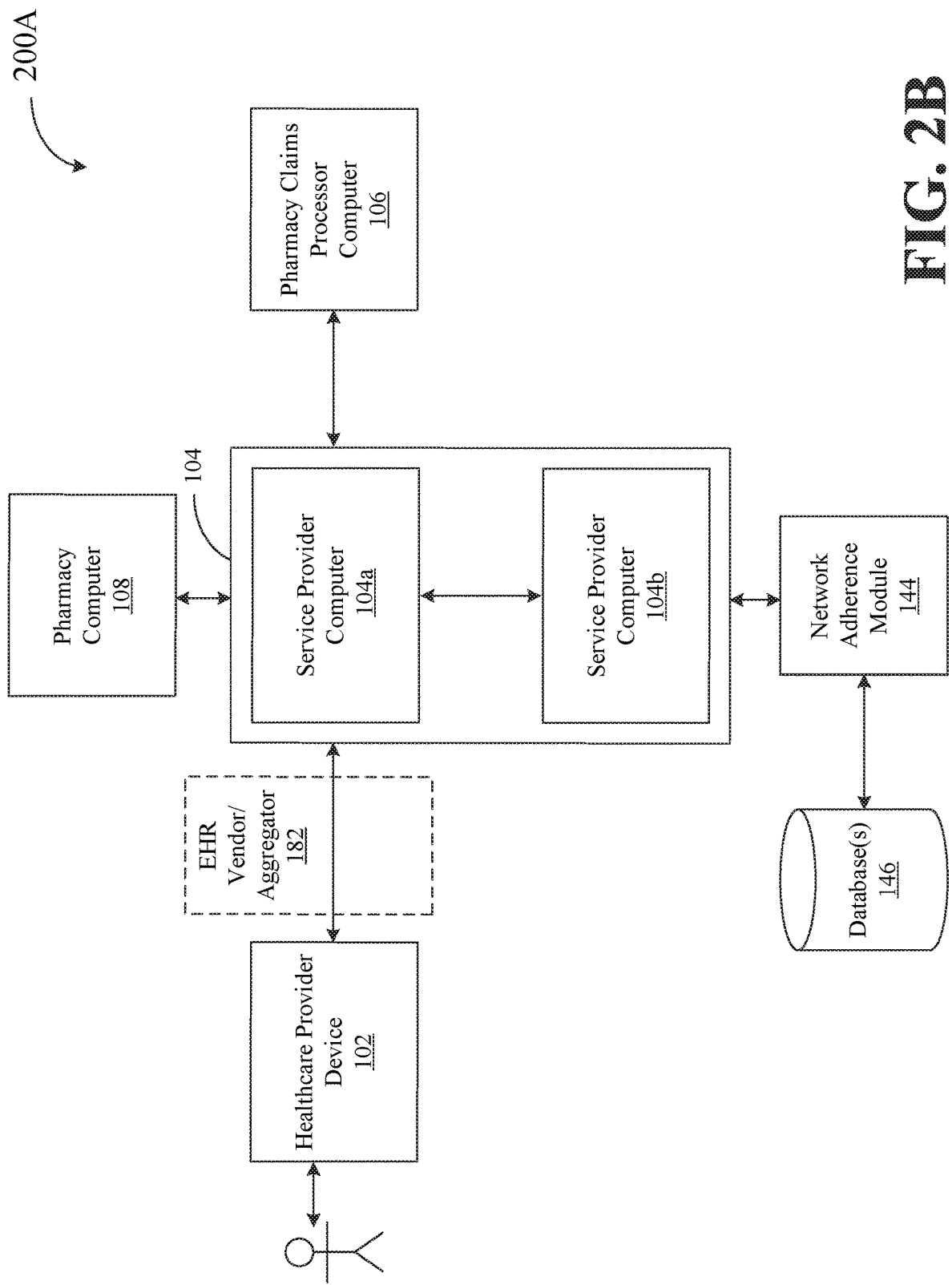
FIG. 2B is a diagram of another example system flow for providing improved adherence monitoring according to an alternative exemplary embodiment.

Likewise, while FIGS. 3A-B, 5, 7, and 8 have been described primarily in conjunction with FIG. 2A, it will be appreciated that variations of FIG. 2A are available. As shown by the system 200A of FIG. 2B, the service provider computer 104 may include two or more distinct service provider computers 104a and 104b that are in communication with each other. These distinct service provider computers 104a and 104b may be owned, operated, and/or located by the same or distinct and wholly-unrelated companies. The service provider computer 104a may be operative with the healthcare provider computer 102, while the service provider computer 104b may be operative with other healthcare provider computers and/or the pharmacy computers. However, the service provider computer 104b may have a data processing arrangement with the service provider computer 104a. Under the data processing arrangement, the service provider computer 104a may be permitted to utilize the adherence monitoring services of the service provider computer 104b, including the operations and use of the network adherence module 144 and the data in the database 146 to identify patient adherence, as discussed above. Accordingly, the services accessible by the service provider computer 104b, may be available to the healthcare provider computer 102 via the service provider computers 104a and 104b.

While certain example embodiments disclosed herein describe the network adherence module 144 as being separate of the service provider computer 104, in alternate embodiments, the network adherence module 144 or the functions that it completes may be part of the service provider computer 104. In those embodiments where the network adherence module 144 is incorporated into the service provider computer 104, and with regard to the methods described above, the elements describing transmitting or receiving between the service provider computer 104 and the network adherence module 144 may be internal transmissions within the service provider computer 104 or may be omitted altogether. Further, while the exemplary embodiments described herein disclose certain steps occurring at the service provider computer 104 and/or the network adherence module 144, in alternative embodiments those steps described with reference to FIGS. 1-8 may alternately be completed at a healthcare provider computer 102, a pharmacy claims processor computer 106, a pharmacy computer 108, a network adherence module 144, any combination thereof, and/or a combination of those devices along with the service provider computer 104. In those alternate embodiments, certain transmission/receiving blocks described above with reference to FIGS. 1-8 may be omitted while others may be added, as understood by one or ordinary skill in the art. The intent being that, in alternate embodiments, any of the devices/computers discussed in FIG. 1 are capable of completing all or any part of the methods described with reference to FIGS. 2A-8.

Accordingly, example embodiments disclosed herein can provide the technical effects of creating a system and method that provides real-time or near real time way to facilitate the improved adherence monitoring system as part of or in-line with the processing of one or more types of healthcare claim requests. In this regard, a notification of a fill may be automatically communicated to a healthcare provider without pharmacy interaction, thus reducing network activity and increasing the efficiency to which the fill notification(s) are communicated.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component that is properly configured. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, are implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a special-purpose machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system, comprising;
at least one memory operable to store computer-executable instructions; and
at least one processor configured to access the at least one memory and execute the computer-executable instructions to:
receive electronically, from a healthcare provider computer for a prescriber via an electronic health records (EHR) intermediary configured to aggregate healthcare transactions originating from a plurality of healthcare provider computers and a plurality of pharmacy claims processor computers, a prescription benefit check request comprising at least one or more patient data, a service identifier, an identifier for a prescribed medication, and one or more prescriber data;
receive electronically, from a pharmacy claims processor computer, a prescription response comprising at least a patient pay amount for the prescribed medication;
in response to receiving the prescription response, access a routing table stored by a service provider computer embodied by a switch or a router to identify the healthcare provider computer from which the prescription benefit check request originated;
electronically direct the communication of a prescription benefit check response comprising at least the patient pay amount from the prescription response to the healthcare provider computer via the EHR intermediary;
receive electronically, from the healthcare provider device via the EHR intermediary, a prescription fill notification request, wherein the prescription fill notification request is generated by the healthcare provider device in response to the healthcare provider receiving the patient pay amount;
monitor, based at least upon the prescription fill notification request, traffic over a network comprising one or more communication channels associated with the EHR intermediary to determine that a pharmacy billing request corresponding to the prescription benefit check request has been submitted to a pharmacy benefits processor by matching at least one of the one or more prescriber data, the one or more patient data or the service identifier stored on the at least one memory in association with the prescription benefit check request to that of a matching pharmacy billing response communicated over the network;
in response to identifying the matching pharmacy billing response, determine a status of the matching pharmacy billing response indicating that the pharmacy billing request was approved by the pharmacy benefits processor;
access the routing table to identify the healthcare provider computer to be notified of medication adherence information associated with the matching pharmacy billing response;
further in response to identifying the matching pharmacy billing response communicated via the EHR intermediary, generate, by at least the service provider computer, a prescription fill notification response comprising at least a prescription fill date, and a pharmacy identification; and
electronically direct communication of the prescription fill notification response to the healthcare provider computer identified by accessing the routing table and via the EHR intermediary, thereby notifying the healthcare provider of medication adherence.

2. The system of claim 1, wherein the prescription fill notification request is automatically communicated by the healthcare provider computer based at least upon the communicated patient pay amount.

3. The system of claim 1, wherein the prescription fill notification request is communicated based upon a physician selection at the healthcare provider computer.

4. The system of claim 1, wherein the processor is further configured to access the at least one memory and execute the computer-executable instructions to:
  identify an EHR vendor corresponding to the EHR intermediary; and
  generate, based at least upon the identified EHR vendor, the prescription fill notification request for the prescribed medication included in the prescription benefit check request.

5. The system of claim 1, wherein the prescription fill notification request is a first fill notification request.

6. The system of claim 1, wherein the prescription fill notification request is a subsequent fill notification request, and wherein the processor is further configured to access the at least one memory and execute the computer-executable instructions to:
  access one or more subsequent fill monitoring criteria comprising at least one of a request to monitor for one or more fills during a specified time period, a request to monitor for a total number of fills, a request to monitor for one or more fills until a refill status for the corresponding medication/product has expired;
  monitor the one or more communication channels for the prescribed medication identified in the prescription benefit check request based at least upon the one or more subsequent fill monitoring criteria; and
  generate a prescription fill notification response for each subsequent fill of the prescribed medication detected.

7. The system of claim 6, wherein the processor is further configured to access the at least one memory and execute the computer-executable instructions to:
  receive electronically, from the healthcare provider computer via the EHR intermediary, a cancelation notice comprising notification to cancel tracking of one or more subsequent fills for the corresponding prescribed medication identified in the prescription benefit check request.

8. The system of claim 1, wherein the processor is further configured to access the at least one memory and execute the computer-executable instructions to:
  generate, based at least upon the prescription benefit check request or the prescription benefit check response, one or more adherence reports based upon the medication identifier for the prescribed medication, wherein an adherence report comprises at least an adherence fill rate for the prescribed medication; and
  electronically direct the communication of the adherence report to the EHR intermediary for distribution to the healthcare provider computer, the pharmacy claims processor computer, or the pharmacy computer.

9. The system of claim 1, wherein the pharmacy claims processor computer is the same as the pharmacy benefits processor, and wherein the determination that the pharmacy billing request was approved by the pharmacy benefits processor is based at least upon the detection of a pharmacy billing response comprising a field status indicator indicating that the request was approved.

10. A computer-implemented method for adherence monitoring, comprising:
  receiving electronically, by the service provider computer associated with a service provider and comprising one or more computer processors from a healthcare provider computer for a prescriber via an electronic health records (EHR) intermediary, an electronic health records (EHR) intermediary configured to aggregate healthcare transactions originating from a plurality of healthcare provider computers and a plurality of pharmacy claims processor computers, a prescription benefit check request comprising at least one or more patient data, a service identifier, an identifier for a prescribed medication, and one or more prescriber data;
  receiving electronically, by the service provider computer from a pharmacy claims processor computer, a prescription response comprising at least a patient pay amount for the prescribed medication;
  in response to receiving the prescription response, accessing a routing table stored by a service provider computer embodied by a switch or a router to identify the healthcare provider computer from which the prescription benefit check request originated;
  transmitting electronically, by the service provider computer, a prescription benefit check response comprising at least the patient pay amount from the prescription response to the healthcare provider computer via the EHR intermediary;
  receiving electronically, by the service provider computer from the healthcare provider device via the EHR intermediary, the prescription fill notification request, wherein the prescription fill notification request is generated by the healthcare provider device in response to the healthcare provider receiving the patient pay amount;
  monitoring, by the service provider computer and based at least upon the prescription fill notification request, traffic over a network comprising one or more communication channels associated with the EHR intermediary to determine that a pharmacy billing request corresponding to the prescription benefit check request has been submitted to a pharmacy benefits processor by matching at least one of the one or more prescriber data, the one or more patient data or the service identifier stored on the at least one memory in association with the prescription benefit check request to that of a matching pharmacy billing response communicated over the network;
  in response to identifying the matching pharmacy billing response, determining, by the service provider computer, a status of the matching pharmacy billing response indicating that the pharmacy billing request was approved by the pharmacy benefits processor;
  accessing the routing table to identify the healthcare provider computer to be notified of medication adherence information associated with the matching pharmacy billing response;
  further in response to identifying the matching pharmacy billing response communicated via the EHR intermediary, generating, by at least the service provider computer, a prescription fill notification response comprising at least a prescription fill date, and a pharmacy identification; and
  transmitting electronically, by service provider computer, the prescription fill notification response to the healthcare provider computer identified by accessing the routing table and via the EHR intermediary, thereby notifying the healthcare provider of medication adherence.

11. The computer-implemented method of claim 10, wherein the prescription fill notification request is automatically communicated by the healthcare provider computer based at least upon the communicated patient pay amount.

12. The computer-implemented method of claim 10, wherein the prescription fill notification request is communicated based upon a physician selection at the healthcare provider computer.

13. The computer-implemented method of claim 10 further comprising:
- identifying, by the service provider computer, an EHR vendor corresponding to the EHR intermediary; and
- generating, by the service provider computer and based at least upon the identified EHR vendor, the prescription fill notification request for the prescribed medication included in the prescription benefit check request.

14. The computer-implemented method of claim 10, wherein the prescription fill notification request is a first fill notification request.

15. The computer-implemented method of claim 10, wherein the prescription fill notification request is a subsequent fill notification request, and further comprises:
- accessing, by the service provider computer, one or more subsequent fill monitoring criteria comprising at least one of a request to monitor for one or more fills during a specified time period, a request to monitor for a total number of fills, a request to monitor for one or more fills until a refill status for the corresponding medication/product has been exhausted;
- monitoring, by the service provider computer, the one or more communication channels for the prescribed medication identified in the prescription benefit check request based at least upon the one or more subsequent fill monitoring criteria; and
- generating, by the service provider computer, a prescription fill notification response for each subsequent fill of the prescribed medication detected.

16. The computer-implemented method of claim 10 further comprising:
- receiving electronically, by the service provider computer from the healthcare provider computer via the EHR intermediary, a cancellation notice comprising notification to cancel tracking of one or more subsequent fills for the corresponding prescribed medication identified in the prescription benefit check request.

17. The computer-implemented method of claim 10 further comprising:
- generating, by the service provider computer based at least upon the prescription benefit check request or the prescription benefit check response, one or more adherence reports for a prescriber based upon the medication identifier for the prescribed medication, wherein an adherence report comprises at least an adherence fill rate for the prescribed medication; and
- transmitting electronically, by the service provider computer, to the EHR intermediary for distribution to the healthcare provider computer, the pharmacy claims processor computer, or the pharmacy computer.

18. The computer-implemented method of claim 10, wherein the pharmacy claims processor computer is the same as the pharmacy benefits processor, and wherein the determination that the pharmacy billing request was approved by the pharmacy benefits processor is based at least upon the detection of a pharmacy billing response comprising a field status indicator indicating that the request was approved.

19. The system of claim 1, wherein monitoring a network comprising one or more communication channels associated with the EHR intermediary is further based on a monitoring window associated with the prescription fill notification request.

* * * * *